US012624092B2

(12) United States Patent
McIlwain et al.

(10) Patent No.: US 12,624,092 B2
(45) Date of Patent: May 12, 2026

(54) COMPOSITIONS AND METHODS FOR MEMBRANE PROTEIN STRUCTURE DETERMINATION

(71) Applicant: THE REGENTS OF THE UNIVERSITY OF MICHIGAN, Ann Arbor, MI (US)

(72) Inventors: Benjamin C. McIlwain, Ann Arbor, MI (US); Randy B. Stockbridge, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 721 days.

(21) Appl. No.: 17/997,720

(22) PCT Filed: May 6, 2021

(86) PCT No.: PCT/US2021/031093

§ 371 (c)(1),
(2) Date: Nov. 1, 2022

(87) PCT Pub. No.: WO2021/226336

PCT Pub. Date: Nov. 11, 2021

(65) Prior Publication Data

US 2023/0174629 A1 Jun. 8, 2023

Related U.S. Application Data

(60) Provisional application No. 63/020,769, filed on May 6, 2020.

(51) Int. Cl.
*C07K 16/00* (2006.01)
*C07K 14/005* (2006.01)
*C07K 16/114* (2026.01)

(52) U.S. Cl.
CPC ........ *C07K 16/1145* (2026.01); *C07K 14/005* (2013.01); *C07K 2317/34* (2013.01); *C07K 2317/55* (2013.01); *C07K 2317/622* (2013.01); *C07K 2319/33* (2013.01)

(58) Field of Classification Search
CPC .............. C07K 16/1063; C07K 14/005; C07K 2317/34; C07K 2317/55; C07K 2319/33; G01N 33/56983; A61K 2039/6056
See application file for complete search history.

(56) References Cited

U.S. PATENT DOCUMENTS

2014/0220107 A1* 8/2014 Kalyanaraman ....... A61K 39/12 424/188.1
2017/0281749 A1 10/2017 Haynes et al.
2021/0393768 A1* 12/2021 Zeichner ................ A61P 31/18

FOREIGN PATENT DOCUMENTS

WO WO 2020/046982 3/2020

OTHER PUBLICATIONS

Molinos-Albert et al (Frontiers in Immunology, 8:1154, 2017) (Year: 2017).*
International Search Report and Written Opinion for PCT/US21/31093. Mailed Aug. 25, 2021. 10 pages.
Borgnia et al., Reconstitution and functional comparison of purified GlpF and AqpZ, the glycerol and water channels from *Escherichia coli*. Proc Natl Acad Sci U S A. Feb. 27, 2001;98(5):2888-93.
Butterwick et al., Cryo-EM structure of the insect olfactory receptor Orco. Nature. Aug. 2018;560(7719):447-452.
Cardoso et al., Broadly neutralizing anti-HIV antibody 4E10 recognizes a helical conformation of a highly conserved fusion-associated motif in gp41. Immunity. Feb. 2005;22(2):163-73.
Cheng et al., A primer to single-particle cryo-electron microscopy. Cell. Apr. 23, 2015;161(3):438-449.
Cymer et al., A single glutamate residue controls the oligomerization, function, and stability of the aquaglyceroporin GlpF. Biochemistry. Jan. 19, 2010;49(2):279-86.
Dang et al., Cryo-EM structures of the TMEM16A calcium-activated chloride channel. Nature. Dec. 21, 2017;552(7685):426-429.
Deep Blue Data repository hosted by the University of Michigan, with unique identifier https://doi.org/10.7302/7ym7-gp78. Retrieved Dec. 13, 2023. 4 pages.
Dreyfus et al., Highly conserved protective epitopes on influenza B viruses. Science. Sep. 14, 2012;337(6100):1343-8.
Dutka et al. Development of "Plug and Play" Fiducial Marks for Structural Studies of GPCR Signaling Complexes by Single-Particle Cryo-EM. Structure, 2019, 27, 1862-1874.
Emsley et al., Features and development of Coot. Acta Crystallogr D Biol Crystallogr. Apr. 2010;66(Pt 4):486-501.
Fang et al., Structure of a prokaryotic virtual proton pump at 3.2 A resolution. Nature. Aug. 20, 2009;460(7258):1040-3.
Flemming et al., Precise mapping of subunits in multiprotein complexes by a versatile electron microscopy label. Nat Struct Mol Biol. Jun. 2010;17(6):775-8.

(Continued)

*Primary Examiner* — Lei Yao
(74) *Attorney, Agent, or Firm* — Casimir Jones, S.C.; Anne M. Reynolds

(57) ABSTRACT

Disclosed herein are compositions and methods for determining the structure of a membrane protein. An epitope from a membrane-proximal external region (MPER) from a viral envelope protein can be grafted on to a variety of diverse membrane proteins to allow for binding structurally characterized antibody fragments, which can aid structural studies.

a

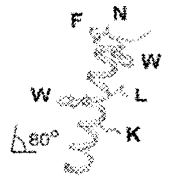

N-LWNWFDITNWLWYIKNL-C
SEQ ID NO: 1

10 Claims, 9 Drawing Sheets

Specification includes a Sequence Listing.

(56) References Cited

OTHER PUBLICATIONS

Fu et al., Structure of a glycerol-conducting channel and the basis for its selectivity. Science. Oct. 20, 2000;290(5491):481-6.
Fu et al., Structure of the membrane proximal external region of HIV-1 envelope glycoprotein. Proc Natl Acad Sci U S A. Sep. 18, 2018;115(38):E8892-E8899.
Giang et al., Human broadly neutralizing antibodies to the envelope glycoprotein complex of hepatitis C virus. Proc Natl Acad Sci U S A. Apr. 17, 2012;109(16):6205-10.
Giannecchini et al., The membrane-proximal tryptophan-rich region in the transmembrane glycoprotein ectodomain of feline immunodeficiency virus is important for cell entry. Virology. Mar. 1, 2004;320(1):156-66.
Goddard et al., UCSF ChimeraX: Meeting modern challenges in visualization and analysis. Protein Sci. Jan. 2018;27(1):14-25.
Gubellini et al., "Labeling of Membrane Complexes for Electron Microscopy" in Membrane Protein Structure and Function Characterization. Springer, 2017, 125-138.
Herzik et al., High-resolution structure determination of sub-100 kDa complexes using conventional cryo-EM. Nat Commun 10, 1032 (2019) 1-9.
Huang et al., Broad and potent neutralization of HIV-1 by a gp41-specific human antibody. Nature. Nov. 15, 2012;491(7424):406-12.
Irimia et al., Crystallographic Identification of Lipid as an Integral Component of the Epitope of HIV Broadly Neutralizing Antibody 4E10. Immunity. Jan. 19, 2016;44(1):21-31.
Irimia et al., Lipid interactions and angle of approach to the HIV-1 viral membrane of broadly neutralizing antibody 10E8: Insights for vaccine and therapeutic design. PLoS Pathog. Feb. 22, 2017;13(2):e1006212.
Kim et al., Application of antihelix antibodies in protein structure determination. Proc Natl Acad Sci U S A. Sep. 3, 2019;116(36):17786-17791.
Koide. Repurposing off-the-shelf antihelix antibodies for enabling structural biology. Proc. Natl. Acad. Sci. U. S. A., 116 (2019), pp. 17611-17613.
Kong et al., Structure of Hepatitis C Virus Envelope Glycoprotein E1 Antigenic Site 314-324 in Complex with Antibody IGH526. J Mol Biol. Aug. 14, 2015;427(16):2617-28.
Krebs et al., Longitudinal Analysis Reveals Early Development of Three MPER-Directed Neutralizing Antibody Lineages from an HIV-1-Infected Individual. Immunity. Mar. 19, 2019;50(3):677-691.e13.
Kwon et al., Optimization of the Solubility of HIV-1-Neutralizing Antibody 10E8 through Somatic Variation and Structure-Based Design. J Virol. Jun. 10, 2016;90(13):5899-5914.
Lee et al., Structure of the Ebola virus envelope protein MPER/TM domain and its interaction with the fusion loop explains their fusion activity. Proc. Natl. Acad. Sci. U. S. A., 2017, 114, pp. E7987-E7996.
Liao et al., Tryptophan-dependent membrane interaction and heteromerization with the internal fusion peptide by the membrane proximal external region of SARS-COV spike protein. Biochemistry. Mar. 10, 2015;54(9):1819-30.
Liebschner et al., Macromolecular structure determination using X-rays, neutrons and electrons: recent developments in Phenix. Acta Crystallogr D Struct Biol. Oct. 1, 2019;75(Pt 10):861-877.
Lomize et al., OPM database and PPM web server: resources for positioning of proteins in membranes. Nucleic Acids Res. Jan. 2012;40(Database issue):D370-6.
Manley et al., Secondary structure and oligomerization of the *E. coli* glycerol facilitator. Biochemistry. Oct. 10, 2000;39(40):12303-11.
Mastronarde. Automated electron microscope tomography using robust prediction of specimen movements. J Struct Biol. Oct. 2005;152(1):36-51.
McCoy et al., Phaser crystallographic software. J Appl Crystallogr. Aug. 1, 2007;40(Pt 4):658-674.
McIlwain et al., Cork-in-Bottle Occlusion of Fluoride Ion Channels by Crystallization Chaperones. Structure, 2018, 26, 635-639 e1.
McMahon et al., Yeast surface display platform for rapid discovery of conformationally selective nanobodies. Nat Struct Mol Biol. Mar. 2018;25(3):289-296.
Molinos-Albert et al., Immunologic Insights on the Membrane Proximal External Region: A Major Human Immunodeficiency Virus Type-1 Vaccine Target. Front Immunol. Sep. 19, 2017:8:1154. 1-12.
Mukherjee et al., Synthetic antibodies against BRIL as universal fiducial marks for single-particle cryoEM structure determination of membrane proteins. Nat Commun. Mar. 27, 2020;11(1):1598. 1-14.
Murin et al., Antibody responses to viral infections: a structural perspective across three different enveloped viruses. Nat Microbiol. May 2019;4(5):734-747.
Murshudov et al., REFMAC5 for the refinement of macromolecular crystal structures. Acta Crystallogr D Biol Crystallogr. Apr. 2011;67(Pt 4):355-67.
Nicely et al., Crystal structure of a non-neutralizing antibody to the HIV-1 gp41 membrane-proximal external region. Nat Struct Mol Biol. Dec. 2010;17(12):1492-4.
Ohi et al., Negative Staining and Image Classification—Powerful Tools in Modern Electron Microscopy. Biol Proced Online. 2004:6:23-34.
Pinto et al., Structural Basis for Broad HIV-1 Neutralization by the MPER-Specific Human Broadly Neutralizing Antibody LN01. Cell Host Microbe. Nov. 13, 2019;26(5):623-637.e8.
Punjani et al., cryoSPARC: algorithms for rapid unsupervised cryo-EM structure determination. Nature Methods, 2017, 14, 290-296.
Rohou et al., CTFFIND4: Fast and accurate defocus estimation from electron micrographs. J Struct Biol. Nov. 2015;192(2):216-21.
Rujas et al., Functional Contacts between MPER and the Anti-HIV-1 Broadly Neutralizing Antibody 4E10 Extend into the Core of the Membrane. J Mol Biol. Apr. 21, 2017;429(8):1213-1226.
Sáez-Cirión et al., Pre-transmembrane sequence of Ebola glycoprotein. Interfacial hydrophobicity distribution and interaction with membranes. FEBS Lett. Jan. 2, 2003;533(1-3):47-53.
Sha et al., Monobodies and other synthetic binding proteins for expanding protein science. Protein Sci. May 2017;26(5):910-924.
Skiniotis et al., Single-particle cryo-electron microscopy of macromolecular complexes. Microscopy (Oxf). Feb. 2016;65(1):9-22.
Soto et al., Developmental Pathway of the MPER-Directed HIV-1-Neutralizing Antibody 10E8. PLoS One. Jun. 14, 2016;11(6):e0157409. 1-21.
Stockbridge et al., A family of fluoride-specific ion channels with dual-topology architecture. Elife. Aug. 27, 2013:2:e01084. 1-14.
Stockbridge et al., Crystal structures of a double-barrelled fluoride ion channel. Nature. Sep. 24, 2015;525(7570):548-51.
Suloway et al., Automated molecular microscopy: the new Leginon system. J Struct Biol. Jul. 2005;151(1):41-60.
Terwilliger et al., Iterative-build OMIT maps: map improvement by iterative model building and refinement without model bias. Acta Crystallogr D Biol Crystallogr. May 2008;64(Pt 5):515-24.
Trefz et al., The GlpF residue Trp219 is part of an amino-acid cluster crucial for aquaglyceroporin oligomerization and function. Biochim Biophys Acta Biomembr. Apr. 2018;1860(4):887-894.
Uchanski et al., Megabodies expand the nanobody toolkit for protein structure determination by single-particle cryo-EM. Nat Methods. Jan. 2021;18(1):60-68.
Wagner et al., SPHIRE-crYOLO is a fast and accurate fully automated particle picker for cryo-EM. Commun. Biol. 2019, 2, 1-13.
Wec et al., Antibodies from a Human Survivor Define Sites of Vulnerability for Broad Protection against Ebolaviruses. Cell. May 18, 2017;169(5):878-890.e15.
Williams et al., MolProbity: More and better reference data for improved all-atom structure validation. Protein Sci. Jan. 2018;27(1):293-315.
Williams et al., Potent and broad HIV-neutralizing antibodies in memory B cells and plasma. Sci Immunol. Jan. 27, 2017;2(7):eaal2200. 1-15.
Wu et al., Fabs enable single particle cryoEM studies of small proteins. Structure. Apr. 4, 2012;20(4):582-92.

(56) References Cited

OTHER PUBLICATIONS

Yeates et al., Development of imaging scaffolds for cryo-electron microscopy. Curr Opin Struct Biol. Feb. 2020:60:142-149.
Zhang et al., Genetic programming of macrophages to perform anti-tumor functions using targeted mRNA nanocarriers. Nat. Commun. 2019, 10, 3974, 1-16.
Zhang. Gctf: Real-time CTF determination and correction. J Struct Biol. Jan. 2016;193(1):1-12.
Zheng et al., MotionCor2: anisotropic correction of beam-induced motion for improved cryo-electron microscopy. Nat Methods. Apr. 2017;14(4):331-332.
Zivanov et al., New tools for automated high-resolution cryo-EM structure determination in RELION-3. Elife 7, Nov. 2015, e42166. 1-22.
Caillat C., et al., "Neutralizing Antibodies Targeting HIV-1 gp41", Viruses, 2020, vol. 12, No. 11, 1210, 19 Pages.
Harrison S.C., "Viral Membrane Fusion", Nature Structural & Molecular Biology, vol. 15, No. 7, Jul. 3, 2008, pp. 690-698.
Riggs P., "Fusion Protein", Brenner's Encyclopedia of Genetics, 2nd Edition, vol. 3, 2013, pp. 134-135.

* cited by examiner

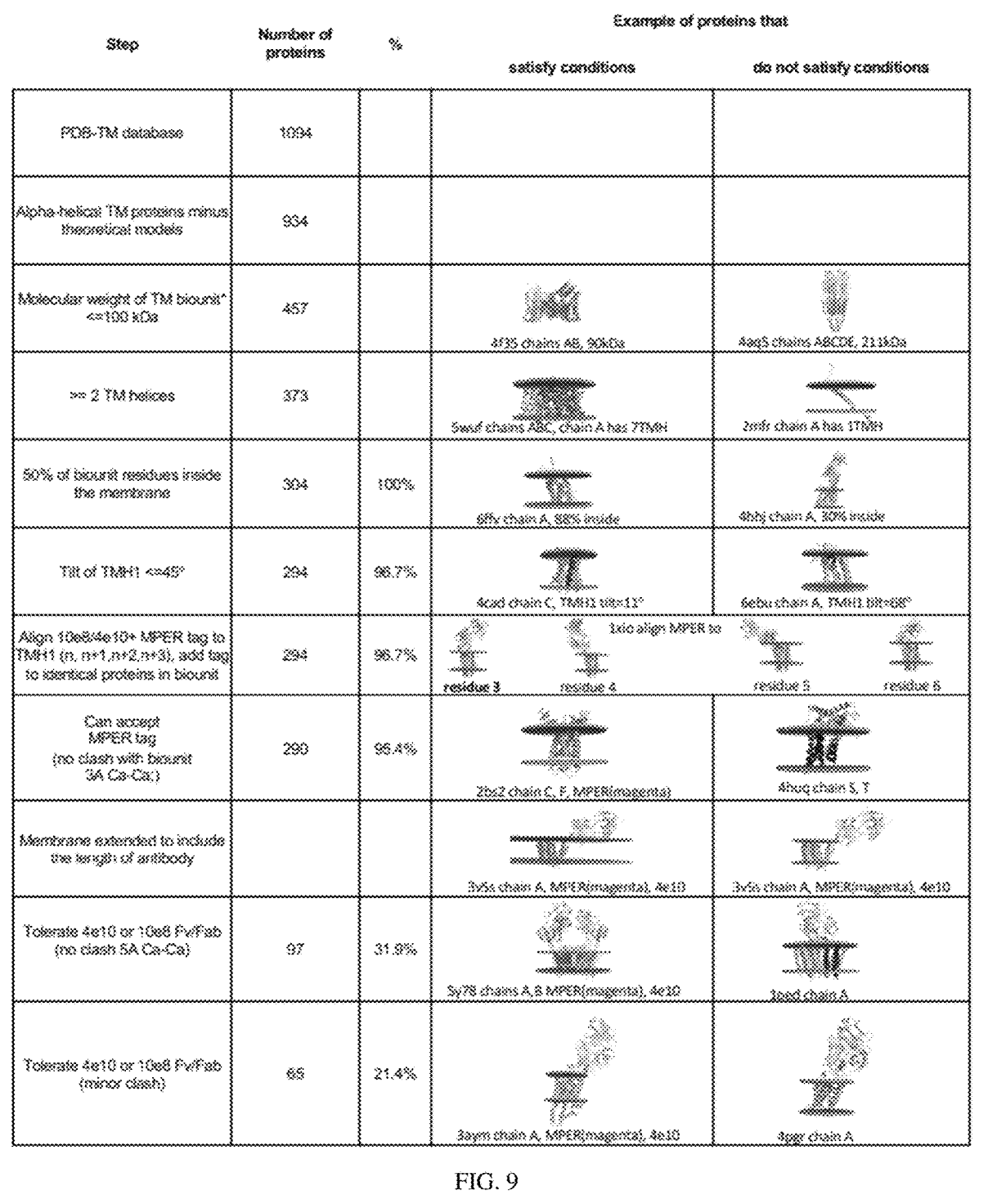

| Step | Number of proteins | % | Example of proteins that | |
|---|---|---|---|---|
| | | | satisfy conditions | do not satisfy conditions |
| PDB-TM database | 1094 | | | |
| Alpha-helical TM proteins minus theoretical models | 934 | | | |
| Molecular weight of TM biounit* <=100 kDa | 457 | |  4f35 chains AB, 90kDa |  4aq5 chains ABCDE, 211kDa |
| >= 2 TM helices | 373 | |  5wuf chains ABC, chain A has 7TMH |  2mfr chain A has 1TMH |
| 50% of biounit residues inside the membrane | 304 | 100% |  6ffv chain A, 88% inside |  4hhj chain A, 30% inside |
| Tilt of TMH1 <=45° | 294 | 96.7% |  4cad chain C, TMH1 tilt=11° |  6ebu chain A, TMH1 tilt=68° |
| Align 10e8/4e10+ MPER tag to TMH1 (n, n+1,n+2,n+3), add tag to identical proteins in biounit | 294 | 96.7% |  residue 3  residue 4 1xio align MPER to |  residue 5  residue 6 |
| Can accept MPER tag (no clash with biounit 3A Ca-Ca;) | 290 | 95.4% |  2bs2 chain C, F, MPER(magenta) |  4huq chain S, T |
| Membrane extended to include the length of antibody | | |  3v5s chain A, MPER(magenta), 4e10 |  3v5s chain A, MPER(magenta), 4e10 |
| Tolerate 4e10 or 10e8 Fv/Fab (no clash 5A Ca-Ca) | 97 | 31.9% |  5y78 chains A,B MPER(magenta), 4e10 |  3oad chain A |
| Tolerate 4e10 or 10e8 Fv/Fab (minor clash) | 65 | 21.4% |  3aym chain A, MPER(magenta), 4e10 |  4pgr chain A |

FIG. 9

SEQUENCE LISTING

<160> NUMBER OF SEQ ID NOS: 17

<210> SEQ ID NO 1
<211> LENGTH: 17
<212> TYPE: PRT
<213> ORGANISM: HIV-1

<400> SEQUENCE: 1

Leu Trp Asn Trp Phe Asp Ile Thr Asn Trp Leu Trp Tyr Ile Lys Asn
1               5                   10                  15

Leu

<210> SEQ ID NO 2
<211> LENGTH: 18
<212> TYPE: PRT
<213> ORGANISM: Ebola virus

<400> SEQUENCE: 2

Asp Asn Asp Asn Trp Trp Thr Gly Trp Arg Gln Trp Ile Ile Ala Gly
1               5                   10                  15

Ile Gly

<210> SEQ ID NO 3
<211> LENGTH: 14
<212> TYPE: PRT
<213> ORGANISM: Influenza B virus
<220> FEATURE:
<221> NAME/KEY: MISC_FEATURE
<222> LOCATION: (3)..(3)
<223> OTHER INFORMATION: Xaa= Q, S, or K
<220> FEATURE:
<221> NAME/KEY: MISC_FEATURE
<222> LOCATION: (9)..(9)
<223> OTHER INFORMATION: Xaa= T or N

<400> SEQUENCE: 3

Thr Gln Xaa Ala Ile Asp Gln Ile Xaa Gly Lys Leu Asn Arg
1               5                   10

<210> SEQ ID NO 4
<211> LENGTH: 17
<212> TYPE: PRT
<213> ORGANISM: Hepatitis C virus

<400> SEQUENCE: 4

Thr Gly Leu Ile His Leu His Gln Asn Ile Val Asp Val Gln Tyr Leu
1               5                   10                  15

Tyr

<210> SEQ ID NO 5
<211> LENGTH: 14

-continued

<212> TYPE: PRT
<213> ORGANISM: Feline Immunodeficiency virus

<400> SEQUENCE: 5

Trp Glu Asp Trp Val Gly Trp Ile Gly Asn Ile Ile Gln Tyr
1               5                   10

<210> SEQ ID NO 6
<211> LENGTH: 22
<212> TYPE: PRT
<213> ORGANISM: Simian immunodeficiency virus

<400> SEQUENCE: 6

Lys Leu Asn Ser Trp Asp Val Phe Gly Asn Trp Phe Asp Leu Ala Ser
1               5                   10                  15

Trp Ile Lys Tyr Ile Gln
            20

<210> SEQ ID NO 7
<211> LENGTH: 12
<212> TYPE: PRT
<213> ORGANISM: SARS-coronavirus
<220> FEATURE:
<221> NAME/KEY: MISC_FEATURE
<222> LOCATION: (2)..(2)
<223> OTHER INFORMATION: Xaa = V or I
<220> FEATURE:
<221> NAME/KEY: MISC_FEATURE
<222> LOCATION: (7)..(7)
<223> OTHER INFORMATION: Xaa = W or Y

<400> SEQUENCE: 7

Tyr Xaa Lys Trp Pro Trp Xaa Val Trp Leu Gly Phe
1               5                   10

<210> SEQ ID NO 8
<211> LENGTH: 155
<212> TYPE: PRT
<213> ORGANISM: Artificial sequence
<220> FEATURE:
<223> OTHER INFORMATION: Synthetic protein sequence

<400> SEQUENCE: 8

Gly His His His His His His Gly Gly Leu Val Pro Arg Gly Ser Ala
1               5                   10                  15

Ser Leu Trp Asn Trp Phe Asp Ile Thr Asn Trp Leu Trp Tyr Ile Lys
            20                  25                  30

Asn Leu Ile Ala Val Ile Ile Gly Gly Ser Val Gly Cys Thr Leu Arg
        35                  40                  45

Trp Leu Leu Ser Thr Arg Phe Asn Ser Leu Phe Pro Asn Leu Pro Pro
    50                  55                  60

Gly Thr Leu Val Val Asn Leu Leu Ala Gly Leu Ile Ile Gly Thr Ala
65                  70                  75                  80

Leu Ala Tyr Phe Leu Arg Gln Pro His Leu Asp Pro Phe Trp Lys Leu
                85                  90                  95

Met Ile Thr Thr Gly Leu Cys Gly Gly Leu Ser Thr Phe Ser Thr Phe
            100                 105                 110

Ser Val Glu Val Phe Ala Leu Leu Gln Ala Gly Asn Tyr Ile Trp Ala
        115                 120                 125

Leu Thr Ser Val Leu Val His Val Ile Gly Ser Leu Ile Met Thr Ala
    130                 135                 140

Leu Gly Phe Phe Ile Ile Thr Ile Leu Phe Ala

-continued 145 150 155

<210> SEQ ID NO 9
<211> LENGTH: 153
<212> TYPE: PRT
<213> ORGANISM: Artificial sequence
<220> FEATURE:
<223> OTHER INFORMATION: Synthetic protein sequence

<400> SEQUENCE: 9

Gly His His His His His His Gly Gly Leu Val Pro Arg Gly Ser Ala
1               5                   10                  15

Ser Leu Trp Asn Trp Phe Asp Ile Thr Asn Trp Leu Trp Tyr Ile Lys
            20                  25                  30

Asn Leu Ile Ala Ile Gly Ile Gly Ala Thr Leu Gly Ala Trp Leu Arg
        35                  40                  45

Trp Val Leu Gly Leu Arg Leu Asn Gly Ala Gly Trp Pro Trp Gly Thr
    50                  55                  60

Leu Thr Ala Asn Leu Val Gly Gly Tyr Leu Ile Gly Val Met Val Ala
65                  70                  75                  80

Leu Ile Ala Ser His Pro Glu Trp Pro Ala Trp Ile Arg Leu Ala Ala
                85                  90                  95

Val Thr Gly Phe Leu Gly Gly Leu Thr Thr Phe Ser Thr Phe Ser Ala
            100                 105                 110

Glu Thr Val Asp Met Leu Glu Arg Gly Val Tyr Ala Thr Ala Ala Ala
        115                 120                 125

Tyr Ala Gly Ala Ser Leu Ala Gly Ser Leu Ala Met Thr Gly Leu Gly
    130                 135                 140

Leu Ala Thr Val Arg Leu Leu Leu Arg
145                 150

<210> SEQ ID NO 10
<211> LENGTH: 304
<212> TYPE: PRT
<213> ORGANISM: Artificial sequence
<220> FEATURE:
<223> OTHER INFORMATION: Synthetic protein sequence

<400> SEQUENCE: 10

Gly His His His His His His Gly Gly Leu Val Pro Arg Gly Ser Ala
1               5                   10                  15

Ser Leu Trp Asn Trp Phe Asp Ile Thr Asn Trp Leu Trp Tyr Ile Lys
            20                  25                  30

Asn Leu Ile Ala Glu Phe Leu Gly Thr Gly Leu Leu Ile Phe Phe Gly
        35                  40                  45

Val Gly Cys Val Ala Ala Leu Lys Val Ala Gly Ala Ser Phe Gly Gln
    50                  55                  60

Trp Glu Ile Ser Val Ile Trp Gly Leu Gly Val Ala Met Ala Ile Tyr
65                  70                  75                  80

Leu Thr Ala Gly Val Ser Gly Ala His Leu Asn Pro Ala Val Thr Ile
                85                  90                  95

Ala Leu Trp Leu Phe Ala Cys Phe Asp Lys Arg Lys Val Ile Pro Phe
            100                 105                 110

Ile Val Ser Gln Val Ala Gly Ala Phe Cys Ala Ala Ala Leu Val Tyr
        115                 120                 125

Gly Leu Tyr Tyr Asn Leu Phe Phe Asp Phe Glu Gln Thr His His Ile
    130                 135                 140

-continued

```
Val Arg Gly Ser Val Glu Ser Val Asp Leu Ala Gly Thr Phe Ser Thr
145                 150                 155                 160

Tyr Pro Asn Pro His Ile Asn Phe Val Gln Ala Phe Ala Val Glu Met
                165                 170                 175

Val Ile Thr Ala Ile Leu Met Gly Leu Ile Leu Ala Leu Thr Asp Asp
            180                 185                 190

Gly Asn Gly Val Pro Arg Gly Pro Leu Ala Pro Leu Leu Ile Gly Leu
        195                 200                 205

Leu Ile Ala Val Ile Gly Ala Ser Met Gly Pro Leu Thr Gly Phe Ala
    210                 215                 220

Met Asn Pro Ala Arg Asp Phe Gly Pro Lys Val Phe Ala Trp Leu Ala
225                 230                 235                 240

Gly Trp Gly Asn Val Ala Phe Thr Gly Gly Arg Asp Ile Pro Tyr Phe
                245                 250                 255

Leu Val Pro Leu Phe Gly Pro Ile Val Gly Ala Ile Val Gly Ala Phe
            260                 265                 270

Ala Tyr Arg Lys Leu Ile Gly Arg His Leu Pro Cys Asp Ile Cys Val
        275                 280                 285

Val Glu Glu Lys Glu Thr Thr Thr Pro Ser Glu Gln Lys Ala Ser Leu
    290                 295                 300


<210> SEQ ID NO 11
<211> LENGTH: 471
<212> TYPE: PRT
<213> ORGANISM: Artificial sequence
<220> FEATURE:
<223> OTHER INFORMATION: Synthetic protein sequence

<400> SEQUENCE: 11

Gly His His His His His His Ser Gly Gly Leu Val Pro Arg Gly Ser
1               5                   10                  15

Gly Ser Leu Trp Asn Trp Phe Asp Ile Thr Asn Trp Leu Trp Tyr Ile
            20                  25                  30

Lys Asn Leu Ile Ala Leu Ile Ile Val Thr Leu Met Val Ser Gly Asn
        35                  40                  45

Ile Met Gly Ser Gly Val Phe Leu Leu Pro Ala Asn Leu Ala Ala Thr
    50                  55                  60

Gly Gly Ile Ala Ile Tyr Gly Trp Leu Val Thr Ile Ile Gly Ala Leu
65                  70                  75                  80

Ala Leu Ser Met Val Tyr Ala Lys Met Ser Ser Leu Asp Pro Ser Pro
                85                  90                  95

Gly Gly Ser Tyr Ala Tyr Ala Arg Arg Cys Phe Gly Pro Phe Leu Gly
            100                 105                 110

Tyr Gln Thr Asn Val Leu Tyr Trp Leu Ala Cys Trp Ile Gly Asn Ile
        115                 120                 125

Ala Met Val Val Ile Gly Val Gly Tyr Leu Ser Tyr Phe Phe Pro Ile
    130                 135                 140

Leu Lys Asp Pro Leu Val Leu Thr Leu Thr Cys Val Ala Val Leu Trp
145                 150                 155                 160

Ile Phe Val Leu Leu Asn Ile Val Gly Pro Lys Met Ile Thr Arg Val
                165                 170                 175

Gln Ala Val Ala Thr Val Leu Ala Leu Val Pro Ile Val Gly Ile Ala
            180                 185                 190

Val Phe Gly Trp Phe Trp Phe Lys Gly Glu Thr Tyr Met Ala Ala Trp
        195                 200                 205
```

-continued

Asn Val Ser Gly Met Asn Thr Phe Gly Ala Ile Gln Ser Thr Leu Asn
    210                 215                 220

Val Thr Leu Trp Ser Phe Ile Gly Val Glu Ser Ala Ser Val Ala Ala
225                 230                 235                 240

Gly Val Val Lys Asn Pro Lys Arg Asn Val Pro Ile Ala Thr Ile Gly
                245                 250                 255

Gly Val Leu Ile Ala Ala Val Cys Tyr Val Leu Ser Thr Thr Ala Ile
            260                 265                 270

Met Gly Met Ile Pro Asn Ala Ala Leu Arg Val Ser Ala Ser Pro Phe
        275                 280                 285

Gly Asp Ala Ala Arg Met Ala Leu Gly Asp Thr Ala Gly Ala Ile Val
    290                 295                 300

Ser Phe Cys Ala Ala Ala Gly Cys Leu Gly Ser Leu Gly Gly Trp Thr
305                 310                 315                 320

Leu Leu Ala Gly Gln Thr Ala Lys Ala Ala Ala Asp Asp Gly Leu Phe
                325                 330                 335

Pro Pro Ile Phe Ala Arg Val Asn Lys Ala Gly Thr Pro Val Ala Gly
            340                 345                 350

Leu Leu Ile Val Gly Val Leu Met Thr Ile Phe Gln Phe Ser Ser Met
        355                 360                 365

Ser Pro Asn Ala Ala Lys Glu Phe Gly Leu Val Ser Ser Val Ser Val
    370                 375                 380

Ile Phe Thr Leu Val Pro Tyr Leu Tyr Thr Cys Ala Ala Leu Leu Leu
385                 390                 395                 400

Leu Gly His Gly His Phe Gly Lys Ala Arg Pro Leu Tyr Leu Leu Ile
                405                 410                 415

Thr Phe Val Ala Phe Val Tyr Cys Ile Trp Ala Val Ile Gly Ser Gly
            420                 425                 430

Ala Lys Glu Val Met Trp Ser Phe Val Thr Leu Met Val Ile Thr Ala
        435                 440                 445

Leu Tyr Ala Leu Asn Tyr Asn Arg Ile His Lys Asn Pro Tyr Pro Leu
    450                 455                 460

Asp Ala Pro Val Lys Gln Asp
465                 470

<210> SEQ ID NO 12
<211> LENGTH: 315
<212> TYPE: PRT
<213> ORGANISM: Artificial sequence
<220> FEATURE:
<223> OTHER INFORMATION: Synthetic protein sequence

<400> SEQUENCE: 12

Gly Trp Ser Cys Ile Ile Leu Phe Leu Val Ala Thr Ala Thr Gly Val
1               5                   10                  15

His Ser Glu Val Arg Leu Val Glu Ser Gly Gly Gly Leu Val Lys Pro
            20                  25                  30

Gly Gly Ser Leu Arg Leu Ser Cys Ser Ala Ser Gly Phe Asp Phe Asp
        35                  40                  45

Asn Ala Trp Met Thr Trp Val Arg Gln Pro Pro Gly Lys Gly Leu Glu
    50                  55                  60

Trp Val Gly Arg Ile Thr Gly Pro Gly Glu Gly Trp Ser Val Asp Tyr
65                  70                  75                  80

Ala Glu Ser Val Lys Gly Arg Phe Thr Ile Ser Arg Asp Asn Thr Lys
                85                  90                  95

-continued

Asn Thr Leu Tyr Leu Glu Met Asn Asn Val Arg Thr Glu Asp Thr Gly
100 105 110

Tyr Tyr Phe Cys Ala Arg Thr Gly Lys Tyr Tyr Asp Phe Trp Ser Gly
115 120 125

Tyr Pro Pro Gly Glu Glu Tyr Phe Gln Asp Trp Gly Gln Gly Thr Leu
130 135 140

Val Ile Val Ser Ser Ala Ser Gly Gly Gly Gly Ser Gly Gly Gly Gly
145 150 155 160

Ser Gly Gly Gly Gly Ser Gly Gly Ser Gly Trp Ser Cys Ile Ile Leu
165 170 175

Phe Leu Val Ala Thr Ala Thr Gly Ser Val Thr Ala Ser Glu Leu Thr
180 185 190

Gln Asp Pro Ala Val Ser Val Ala Leu Lys Gln Thr Val Thr Ile Thr
195 200 205

Cys Arg Gly Asp Ser Leu Arg Ser His Tyr Ala Ser Trp Tyr Gln Lys
210 215 220

Lys Pro Gly Gln Ala Pro Val Leu Leu Phe Tyr Gly Lys Asn Asn Arg
225 230 235 240

Pro Ser Gly Ile Pro Asp Arg Phe Ser Gly Ser Ala Ser Gly Asn Arg
245 250 255

Ala Ser Leu Thr Ile Thr Gly Ala Gln Ala Glu Asp Glu Ala Asp Tyr
260 265 270

Tyr Cys Ser Ser Arg Asp Lys Ser Gly Ser Arg Leu Ser Val Phe Gly
275 280 285

Gly Gly Thr Lys Leu Thr Val Leu Ser Gln Pro Lys Ala Ala Glu Asn
290 295 300

Leu Tyr Phe Gln Ser His His His His His His
305 310 315

<210> SEQ ID NO 13
<211> LENGTH: 15
<212> TYPE: PRT
<213> ORGANISM: Artificial sequence
<220> FEATURE:
<223> OTHER INFORMATION: Synthetic protein sequence

<400> SEQUENCE: 13

Leu Thr Ile Ala Pro Leu Ile Ala Ile Gly Ile Gly Ala Thr Leu
1 5 10 15

<210> SEQ ID NO 14
<211> LENGTH: 26
<212> TYPE: PRT
<213> ORGANISM: Artificial sequence
<220> FEATURE:
<223> OTHER INFORMATION: Synthetic protein sequence

<400> SEQUENCE: 14

Leu Trp Asn Trp Phe Asp Ile Thr Asn Trp Leu Trp Tyr Ile Lys Asn
1 5 10 15

Leu Ile Ala Ile Gly Ile Gly Ala Thr Leu
20 25

<210> SEQ ID NO 15
<211> LENGTH: 27
<212> TYPE: PRT
<213> ORGANISM: Artificial sequence
<220> FEATURE:
<223> OTHER INFORMATION: Synthetic protein sequence -continued

```
<400> SEQUENCE: 15

Leu Trp Asn Trp Phe Asp Ile Thr Asn Trp Leu Trp Tyr Ile Lys Asn
1               5                   10                  15

Leu Leu Ile Ala Ile Gly Ile Gly Ala Thr Leu
            20                  25


<210> SEQ ID NO 16
<211> LENGTH: 28
<212> TYPE: PRT
<213> ORGANISM: Artificial sequence
<220> FEATURE:
<223> OTHER INFORMATION: Synthetic protein sequence

<400> SEQUENCE: 16

Leu Trp Asn Trp Phe Asp Ile Thr Asn Trp Leu Trp Tyr Ile Lys Asn
1               5                   10                  15

Leu Ile Leu Ile Ala Ile Gly Ile Gly Ala Thr Leu
            20                  25


<210> SEQ ID NO 17
<211> LENGTH: 29
<212> TYPE: PRT
<213> ORGANISM: Artificial sequence
<220> FEATURE:
<223> OTHER INFORMATION: Synthetic protein sequence

<400> SEQUENCE: 17

Leu Trp Asn Trp Phe Asp Ile Thr Asn Trp Leu Trp Tyr Ile Lys Asn
1               5                   10                  15

Leu Ala Ile Leu Ile Ala Ile Gly Ile Gly Ala Thr Leu
            20                  25
```

COMPOSITIONS AND METHODS FOR MEMBRANE PROTEIN STRUCTURE DETERMINATION

CROSS-REFERENCE TO RELATED APPLICATIONS

This application is a U.S. national stage filing of International Patent Application No. PCT/US2021/031093, filed on May 6, 2021, which claims priority to U.S. Provisional Patent Application No. 63/020,769, filed on May 6, 2020, the entire contents of each of which are fully incorporated herein by reference.

STATEMENT REGARDING FEDERALLY SPONSORED RESEARCH

This invention was made with government support under GM128768 awarded by the National Institutes of Health. The government has certain rights in the invention.

SEQUENCE LISTING

The text of the computer readable sequence listing filed herewith, titled "38317-601_Sequence_Listing_ST25", created May 6, 2021, having a file size of 16,274 bytes, is hereby incorporated by reference in its entirety.

BACKGROUND

Limited tools exist for the structural analysis of small membrane proteins (e.g., those less than 200 kDa or 100 kDa). A biochemically tractable protein might not crystallize due to lack of lattice-forming crystal contacts. At the same time, such proteins are too small and indistinct to be visualized with electron microscopy (EM) and often suffer from low signal-to-noise-induced misalignment in a disordered detergent micelle (Herzik et al. *Nat. Commun.* 10, 1-9 (2019)). One strategy to overcome these challenges is to use soluble chaperone proteins such as antibody fragments. Two such fragments are the single-chain variable-domain fragment (scFv) and fragment antigen-binding (Fab).

scFv fragments are composed of a single 25-kDa unit, the variable domain of an antibody joined by a linker; scFvs are often extremely rigid, leading to highly ordered crystals. Fabs have been used in membrane protein structural biology, primarily in X-ray crystallography. Antibody fragments also been used in high resolution electron microscopy (Wu et al. Structure 20, 582-592 (2012)). Fab fragments have two 25-kDa units, the constant and variable domains, which are arranged as an open clamshell through two elbow regions. The elbow-like hinge region between these units appears as a hole—a feature particularly useful for high-resolution particle alignment from EM images of particles in either vitrified ice or negative stain. Additionally, the 50-kDa proteins are an excellent strategy to increase the effective size of complexed particles, and can overcome problems with preferred particle orientation, reducing anisotropy of the dataset by improving the distribution of Euler angles of the particles in single particle cryo-EM analysis (Dang et al. *Nature,* 552, 426-429 (2017); Butterwick et al. *Nature* 560,447-485 (2018)). Antibody fragments that bind targets specifically can also be used as localization tags, which are useful for interpreting low-resolution EM density maps in order to unambiguously localize regions of the protein and map macromolecule topology.

However, several non-trivial limitations accompany the use of antibody fragments for structural biology. Antibodies with binding specificities to a target protein are generally discovered by immunization of the target protein in small laboratory animals. The requisite immunization and antibody-discovery campaign can take several months, and it can be difficult to generate antibodies against small membrane proteins, which can be poorly immunogenic. Antibody fragments discovered by this method sometimes lack stability or biochemical tractability, and flexible loops with limited utility for structural studies are often recognized. Additional complications arise if antibodies are desired against a structural target in a particular confirmation or a substrate-occupied state. The development of combinatorial libraries of antibody-like proteins, such as megabodies, nanobodies, and monobodies, has addressed some of these problems, allowing binder discovery via phage or yeast display (Sha et al. *Protein Sci.,* 26 (2017), pp. 910-924; Uchanski et al. *Nat. Methods,* 18 (2021), pp. 60-68; McMahon et al. *Nat. Struct. Mol. Biol.,* 25 (2018), pp. 289-296). However, these approaches still require a discovery campaign and tailored approaches to select binders against a desired epitope. Identification of "plug-and-play" chaperones or fiducial markers that can be used for many different protein targets has been a recent focus of protein engineering (Kim et al. *Proc. Natl. Acad. Sci.,* 116 (2019), pp. 17786-17791; Dutka et al. Structure, 27 (1862-74) (2019), Article e7; Yeates et al. *Curr. Opin. Struct. Biol.,* 60 (2020), pp. 142-149; Mukherjee et al. *Nat. Commun.,* 11 (2020), p. 1598). In particular, anti-helix antibodies that recognize a short, linear epitope with α-helical secondary structure have been put forth as a promising avenue for the development of unobtrusive, broadly applicable, high-affinity Fab recognition (Kim 2019; Koide *Proc. Natl. Acad. Sci. U.S.A,* 116 (2019), pp. 17611-17613).

Such an approach has special potential for determining the structures of small membrane proteins. A general drawback of the plug-and-play approach is that chaperone markers need to be fixed relative to the target protein to be useful as fiducials for structural determination, but it has not been clear how to fix such chaperone markers in the absence of structural information. Thus, it is difficult to generate a useful chaperone marker by merely appending a tag to the target membrane protein, as the introduced tag will be structurally flexible relative to the target. For this reason, strategies to link small soluble proteins like maltose binding protein, lysozyme, or YFP to a target have not been broadly adopted (Skiniotis et al. *Microscopy* (*Oxf*), 65 (2016), pp. 9-22).

SUMMARY

Disclosed herein is an approach to graft a defined epitope directly onto a target membrane protein, wherein the epitope can bind to publicly available, structurally characterized antibodies or to a single antibody that can be used against multiple different membrane protein targets, offering a convenient and biochemically-tractable method to complex membrane proteins with antibody fragments. Structural determination can be carried out by both X-ray crystallography and electron microscopy. This approach offers the opportunity to use "off-the-shelf" antibodies that will recognize an epitope that can be used with a variety of membrane proteins. This approach may be particularly useful for membrane proteins that are among the most difficult to study using structural biology techniques, namely small helical bundles that are almost entirely embedded within a membrane.

The present disclosure provides a complex comprising:

(a) a fusion protein comprising formula A-B, wherein:

A is a peptide having at least 80% identity to a membrane-proximal external region (MPER) sequence from a viral envelope protein; and B is membrane protein; and (b) an antibody fragment that binds to the peptide A.

In some embodiments, the viral envelope protein is selected from human immunodeficiency virus gp41, Ebola virus GP2, and influenza HA1. In some embodiments, the viral envelope protein is human immunodeficiency virus gp41.

In some embodiments, A is a peptide of SEQ ID NO: 1, or a variant thereof having 1, 2, or 3 amino acid substitutions compared to SEQ ID NO: 1. In some embodiments, one or more of the 1, 2, or 3 amino acid substitutions is a conservative substitution. In some embodiments, A is a peptide of SEQ ID NO: 1.

In some embodiments, B is a membrane protein having a molecular weight of less than 200 kDa.

In some embodiments, A is attached to the N-terminus of the membrane protein B.

In some embodiments, the antibody fragment is selected from the group consisting of 10E8, LNO1, DH511, VRC42, PGZL1, and 4E10. In some embodiments, the antibody fragment is 10E8 or VRC42.

The present disclosure also provides a method of determining the structure of a membrane protein, comprising:

(a) providing a complex of any one of claims 1-10; and (b) determining the structure of the complex, to thereby determine the structure of the membrane protein.

In some embodiments, the structure of the complex is determined by X-ray crystallography. In some embodiments, the method further comprises a step of forming a crystal of the complex.

In some embodiments, the structure of the complex is determined by electron microscopy. In some embodiments, the electron microscopy is cryo-electron microscopy.

The present disclosure also provides a use of a peptide having at least 80% identity to a membrane-proximal external region (MPER) sequence from a viral envelope protein for protein structure analysis by fusing the peptide a membrane protein. In some embodiments, the peptide is fused to the N-terminus of the membrane protein.

BRIEF DESCRIPTION OF THE DRAWINGS

FIG. 9 shows pipeline for modeling MPER-membrane protein fusions and antibody fragment binding.

DETAILED DESCRIPTION

The present disclosure relates to compositions and methods for determining the structure of a membrane protein, such as a small membrane protein (e.g., less than 200 kDa). To harness the utility of Fab fragments to aid membrane protein structure determination, while minimizing limitations, an epitope from a membrane-proximal external region (MPER) of a viral envelope protein is grafted on to a variety of diverse membrane proteins. This allows for binding of publicly available, structurally characterized antibody fragments to aid structural studies.

Figures 1A, 1B, 1C:
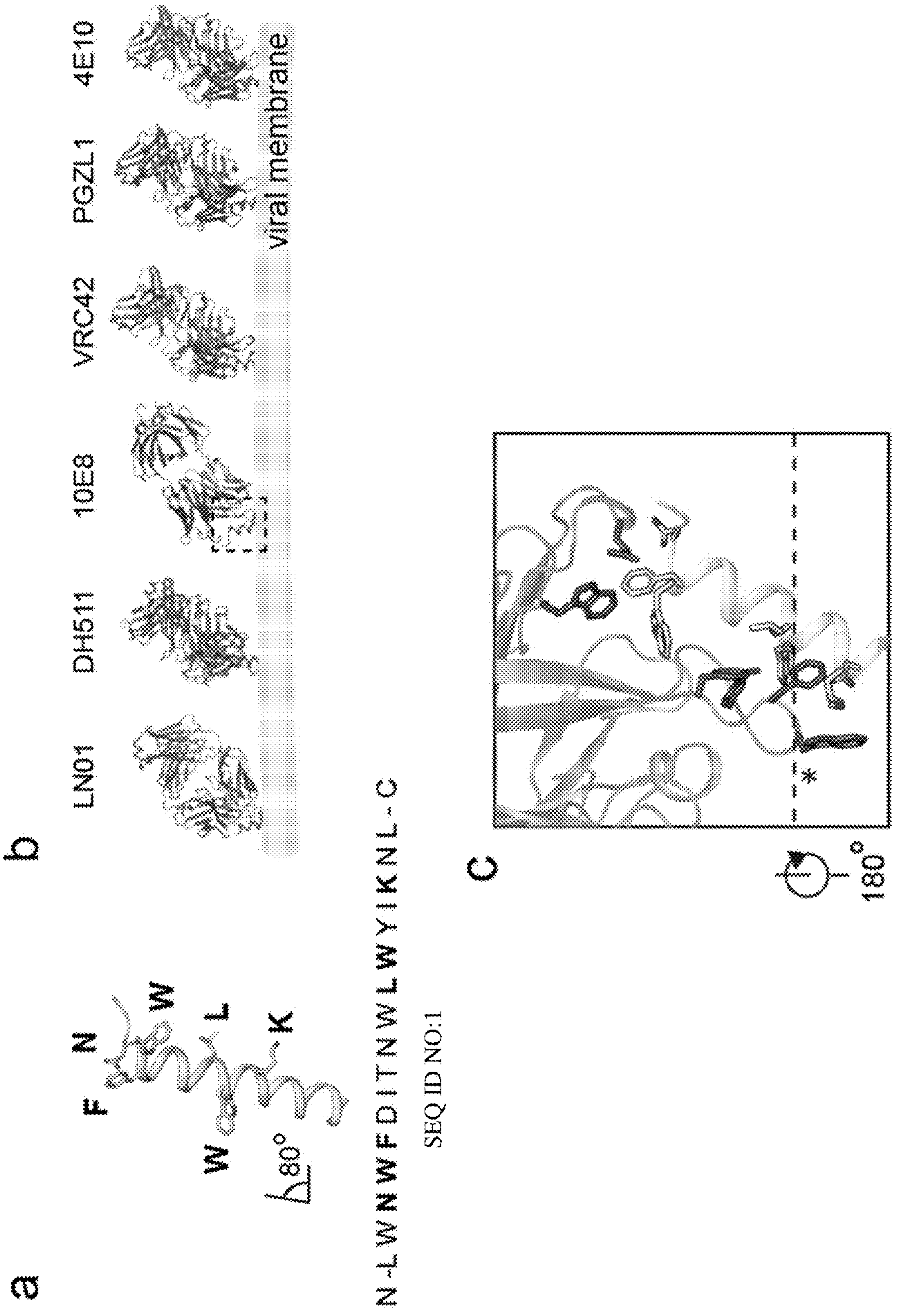
FIGS. 1*a*-1*c* show how the membrane proximal external region (MPER) of the HIV-1 viral envelope protein, gp41, can bind to several structurally-characterized antibody fragments: (a) the HIV-1 gp41 MPER epitope sequence, and structure shown relative to the plane of the membrane, with residues critical for binding the antibody 10E8 shown as sticks and displayed in bold in the sequence; (b) structures of Fab fragments bound to the MPER epitope (LN01 pdb: 6SNC; DH501 pdb: 6PB3; 10E8 pdb: 5JNY; VRC42 pdb: 6MTQ; PGZL1 pdb: 6041; 4E10 pdb: 1T7G), with MPER helices all oriented in the same way for each structure, with the approximate position of the viral membrane shown as a slab; (c) view of MPER epitope/10E8v4 binding interface, with residues involved in antibody binding shown as sticks, and * denoting a Trp (W) residue that interacts with membrane lipids, and the approximate position of viral membrane shown as a dashed line.

The MPER of a viral envelope protein is a hotspot for recognition by broadly neutralizing antibodies. For example, in the human immunodeficiency virus 1 (HIV-1) viral envelope protein gp41, the MPER includes about 20 amino acids forming two short helical segments, one more distal and the other more proximal to the membrane (Uniprot ID: Q70626). The more proximal helix extends relatively perpendicular from the plane of the membrane (FIG. 1*a*) (Fu et al. *Proc. Natl. Acad. Sci. U.S.A.* 115, E8892-E8899 (2018); Irimia et al. *PLoS Pathog.* 13, e1006212 (2017)). This region is a hotspot for recognition by broadly neutralizing antibodies, and due to the importance of this epitope in structural immunology, several MPER-Fab complexes have been characterized in biochemical and structural detail (Nicely et al. *Nat. Struct. Mol. Biol.* 17, 1492 (2010); Zhang et al. *Nat. Commun.* 10, 1-16 (2019); Krebs et al. *Immunity* 50, 677-691 e13 (2019); Williams et al. *Sci. Immunol.* 2 (7) eaal2200 (2017); Rujas et al. *J. Mol. Biol.* 429, 1213-1226 (2017); Pinto et al. *Cell Host Microbe* 26, 623-637. e8 (2019); Huang et al. *Nature* 491, 406-412 (2012)) (FIGS. 1*b* and 1*c*). These antibody fragments bind to the extramembrane tryptophan-rich MPER in various poses, and usually have long, hydrophobic loops to facilitate binding (Zhang et al. *Nat. Commun.* 10, 1-16 (2019)). Although representative antibodies are able to bind to the isolated MPER peptide, in the full biological context, the membrane itself also comprises part of the epitope (Irimia 2017; Irimia et al. *Immunity* 44, 21-31 (2016); Krebs 2019; Pinto 2019) and contributes to the binding affinity, which is typically in the low nanomolar range.

Disclosed herein are complexes comprising a fusion protein and an antibody fragment. In the fusion protein, a membrane protein is fused to a peptide having a sequence corresponding to that of an MPER of a viral envelope protein (or a variant thereof). Grafting of the MPER peptide onto the membrane protein provides a defined docking site for an MPER-targeting antibody fragment, which can aid in structural studies of the membrane protein, either by X-ray crystallography or by electron microscopy.

This strategy is particularly useful for proteins that are among the most difficult to study using current structural biology techniques: small helical bundles that are almost entirely embedded within the membrane. N-terminal signal peptides or membrane localization sequences should be compatible with this approach, as long as they are proteolytically cleaved prior to Fab binding, as has been done with the N-terminal purification tags in the present experiments. In case shown in the Examples, MPER tags did not appear to influence protein stability.

There are several other contemplated advantages to this approach. First, the biochemical properties of the MPER/antibody combinations described herein are particularly felicitous for structural biology of membrane proteins. As a contiguous extension of the N-terminal transmembrane helix of a target protein, the epitope is a structurally defined and rigid docking site for the antibody fragments. Negative stain 2-D class averages of the MPER-Fluc/10E8v4 construct, described in the Examples, highlight the rigidity of the complex: although the two Fab binding sites are at opposite ends of the elongated complex, both target-bound Fab fragments align well, with notably well-defined holes between the constant and variable domains of the Fab fragments.

Second, the helical epitope is entirely discrete from the target protein and requires no alteration of native protein sequence, aside from the N-terminus. Thus, introducing this epitope is a milder maneuver than other strategies that depend on, for example, replacement of one of the helices of the target protein with a transmembrane epitope (Kim 2019; Mukherjee 2020). Moreover, the substrate occupancy of the binding site, as well as co-transported ions should not influence the complexing of protein to antibody fragments, introducing the ability to explore multiple protein conformations and ion-occupied states with the same target-protein construct and antibody Fab fragment.

Third, a number of different antibodies have been identified that bind to the MPER epitope in varying orientations. Many known and characterized antibody fragments can be screened for target binding and effect on oligomerization, behavior in vitreous ice, and ability to form stable crystal contacts. In addition, the Fab fragments could be further engineered to improve their characteristics for structural biology applications, for example by introducing mutations to lock the elbow hinge region of the Fab fragment (Koide 2019). In addition, other viral spike proteins possess sequences analogous to the HIV-1 gp41 MPER that are hotspots for antibody recognition (Giang et al. *Proc. Natl. Acad. Sci. U.S.A,* 109 (2012), pp. 6205-6210; Dreyfus et al. *Science,* 337 (2012), pp. 1343-1348; Lee et al. *Proc. Natl. Acad. Sci. U.S.A,* 114 (2017), pp. E7987-E7996; Murin et al. *Nat. Microbiol.,* 4 (2019), pp. 734-747). While examples herein focus on the HIV-1 MPER epitope because its interactions with multiple Fab fragments have been well-characterized, similar helical epitopes from other viral spike proteins should be similarly useful as transplantable epitopes for Fab recognition.

Fourth, the antibodies that recognize the MPER epitope have innate affinity for the membrane, and this approach is therefore compatible—and even improved—when membrane mimetics like nanodiscs are used. The antibodies that recognize the MPER epitope also engage the membrane via specific interactions (Irimia 2017; Krebs 2019; Pinto 2019; Irimia 2016), thus reconstitution of the membrane protein into nanodiscs might expand the recognition surface and further improve the rigidity of the Fab-membrane protein complex.

Fifth, this approach allows one to choose between the larger, more featureful Fabs or the smaller, easily produced short chain variable fragments (scFvs). The utility of the scFvs for X-ray crystallography and as a visible marker for negative stain electron microscopy is demonstrated herein. In addition, despite the absence of the "hole" between the constant and variable domains of the antibody fragment, scFvs also find use as an electron microscopy label for interpreting low-resolution EM density maps. Whereas X-ray crystallography has the advantage of labeling with heavy atoms, EM benefits from the introduction of protein labels to unambiguously localize regions of the protein (Bubellini et al. "Labeling of Membrane Complexes for Electron Microscopy" in *Membrane Protein Structure and Function Characterization* 125-138 (Springer, 2017)) and map macromolecule topology (Flemming et al. *Nat. Struct. Mol. Biol.* 17, 775-778 (2010)). scFvs will be especially useful for X-ray crystallography applications, since they do not suffer from flexibility in the hinge region. scFvs are recombinantly expressed in bacteria, significantly reducing the time and costs associated with using MPER-binding antibody fragments as crystallization chaperones, cryo-EM fiducial markers, or localization tags.

Accordingly, in some embodiments, the disclosure provides a complex comprising:

(a) a fusion protein having formula A-B, wherein:
  A is a peptide having at least 80% identity to a membrane-proximal external region (MPER) sequence from a viral envelope protein; and
  B is membrane protein; and
(b) an antibody fragment that binds to the peptide A.

As used herein, the term "membrane-proximal external region" or "MPER" refers to a conserved peptide sequence in a viral envelope protein, located near the viral envelope surface.

In some embodiments, A is a peptide having 14, 15, 16, 17, 18, 19, or 20 amino acids. In some embodiments, A is a peptide having 17 amino acids.

In some embodiments, A is a peptide having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an MPER sequence from a viral envelope protein.

In some embodiments, the viral envelope protein is the human immunodeficiency virus (HIV-1) viral envelope protein gp41. The HIV-1 gp41 MPER is a 17-residue α-helical extension of the N-terminal transmembrane helix (SEQ ID NO: 1). Accordingly, in some embodiments, A has at least 80% identity to SEQ ID NO: 1. In some embodiments, A is a peptide having SEQ ID NO: 1, or a variant thereof having 1, 2, or 3 amino acid substitutions compared to SEQ ID NO: 1. In some embodiments, one or more of the amino acid substitutions is a conservative substitution. As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine(S) and Threonine (T); and
8) Cysteine (C) and Methionine (M).

In some embodiments, A is a peptide of SEQ ID NO: 1.

In some embodiments, the viral envelope protein is the GP2 subunit of the Ebola virus surface transmembrane glycoprotein (EboV GP2), and the MPER has a sequence set forth in SEQ ID NO: 2 (see, e.g., Sácz-Cirión et al. *FEBS Lett.* 533 (1), 47-53 (2003)). In some embodiments, the viral envelope protein is hemagglutinin (HA) from the influenza B virus, and the MPER has a sequence set forth in SEQ ID NO: 3 (see, e.g., Giang et al. *Proc. Natl. Acad. Sci.* 109 (16), 6205-6210 (2012)). In some embodiments, the viral envelope protein is glycoprotein complex E1/E2 from the hepatitis C virus; in some such embodiments, the MPER has a sequence set forth in SEQ ID NO: 4. In some embodiments, the viral envelope protein is gp36 from the feline immunodeficiency virus (FIV), and the MPER has a sequence set forth in SEQ ID NO: 5 (see, e.g., Giannecchini et al. *Virology* 320 (1), 156-166 (2004)). In some embodiments, the viral envelope protein is gp41 from the simian immunodeficiency virus (SIV), and the MPER has a sequence set forth in SEQ ID NO: 6. In some embodiments, the viral envelope protein is HR2 from the SARS coronavirus (SARS-CoV) or the SARS coronavirus 2 (SARS-CoV-2), and the MPER has a sequence set forth in SEQ ID NO: 7 (see, e.g., Liao et al. *Biochemistry* 54 (9), 1819-1830 (2015)). Accordingly, in some embodiments, A has at least 80% identity to SEQ ID NO: 2, SEQ ID NO: 3, SEQ ID NO: 4, SEQ ID NO: 5, SEQ ID NO: 6, or SEQ ID NO: 7. In some embodiments, A is a peptide having SEQ ID NO: 1, SEQ ID NO: 2, SEQ ID NO: 3, SEQ ID NO: 4, SEQ ID NO: 5, SEQ ID NO: 6, or SEQ ID NO: 7, or a variant of any thereof having 1, 2, or 3 amino acid substitutions. In some embodiments, one or more of the amino acid substitutions is a conservative substitution.

B is a membrane protein. As used herein, the term "membrane protein" refers to a protein having at least one segment that that spans a biological membrane (e.g., a cell membrane). A membrane protein may have one or more α-helical transmembrane sequences, or may have a β-barrel structure spanning the membrane. The term "membrane protein" also includes sequences in which one or more amino acids, such as terminal amino acids (e.g., N-terminal amino acids) are removed from the native protein sequence (e.g., to provide for optimal attachment of the MPER peptide A, as described herein). In particular embodiments, the membrane protein comprises one or more transmembrane α-helices.

The MPER peptide A can be fused to the terminus of any membrane protein that is of interest for structural studies. In some embodiments, B is a membrane protein having a molecular weight of less than about 200 kDa, or a molecular weight of less than about 100 kDa. For example, B may be a membrane protein having a molecular weight of less than about 200 kDa, less than about 195 kDa, less than about 190 kDa, less than about 185 kDa, less than about 180 kDa, less than about 175 kDa, less than about 170 kDa, less than about 165 kDa, less than about 160 kDa, less than about 155 kDa, less than about 150 kDa, less than about 145 kDa, less than about 140 kDa, less than about 135 kDa, less than about 130 kDa, less than about 125 kDa, less than about 120 kDa, less than about 115 kDa, less than about 110 kDa, less than about 105 kDa, less than about 100 kDa, less than about 95 kDa, less than about 90 kDa, less than about 85 kDa, less than about 80 kDa, less than about 75 kDa, less than about 70 kDa, less than about 65 kDa, less than about 60 kDa, less than about 55 kDa, less than about 50 kDa, less than about 45 kDa, less than about 40 kDa, less than about 35 kDa, less than about 30 kDa, less than about 25 kDa, less than about 20 kDa, less than about 15 kDa, less than about 10 kDa, less than about 5 kDa, or less than about 2.5 kDa.

In some embodiments, A is attached to the N-terminus of the membrane protein B. The positioning of the peptide A on the membrane protein B is an important experimental consideration. One skilled in the art will appreciate that the antibody binding surface will rotate by about 100° for each amino acid shift along the membrane protein transmembrane helix 1. Accordingly, in some embodiments, A is directly attached to the N-terminus of the membrane protein B. In other embodiments, A is attached to the membrane protein B at the n+1, n+2, n+3, n+4, or the n+5 position, or the like. Optimal positioning of the MPER peptide A on any given membrane protein B can be experimentally determined by systematically shifting the register of the fusion (see, e.g., FIG. 3). Binding can be evaluated, for example, by gel filtration chromatography. If complexes do not elute as a single peak, they may not be suitable for further structural work, whereas those eluting as single peaks would be suitable for structural investigation.

A variety of different antibody fragments can be used to form the complex. MPER sequences are known to be targets for broadly neutralizing antibodies, and numerous antibody fragments that bind to MPERs are known. For example, antibody fragments that bind to the HIV-1 gp41 MPER include 10E8, LNO1, DH511, VRC42, PGZL1, and 4E10. Antibodies that bind to the EboV Gp2 MPER include ADI-16061 (Wec et al. *Cell* 169, 878-890 (2017)). Antibodies that bind to influenza B HA include CR9114 (Dreyfus et al. *Science* 337, 1343-1348 (2012)). Antibodies that bind to the hepatitis C glycoprotein subunit E1 include IGH526 (Kong et al. *J. Mol. Biol.* 427, 2617-2628 (2015)). Antibodies that bind to the hepatitis C glycoprotein E2 include AR4A (Giang et al. *Proc. Natl. Acad. Sci.* 109 (16), 6205-6210 (2012)). Other antibodies and antibody fragments that bind to MPERs have been described (Molinos-Albert et al. *Front Immunol.* 8, 1154 (2017). Each of these references is herein incorporated by reference in its entirety. In some embodiments, the antibody fragment is selected from 10E8, LNO1, DH511, VRC42, PGZL1, and 4E10, or a variant of any thereof.

The antibody fragment may also be a single chain variable fragment based on a known antibody fragment that binds to an MPER sequence. As only the variable domain is responsible for antigen binding, the heavy and light chains of the variable domain can be concatenated by a linker of about 10-25 amino acids. The linker may be rich in glycine residues for flexibility, as well as serine and/or threonine residues for solubility. The linker may connect the N-terminus of the heavy chain to the C-terminus of the light chain, or may connect the C-terminus of the heavy chain to the N-terminus of the light chain. For example, disclosed herein is a single-chain variable domain fragment based on the 10E8 Fab fragment, with the heavy and light chains concatenated via a $(Gly_3Ser)_4$ linker. This scFv was periplasmically expressed in *E. coli* and has the sequence set forth in SEQ ID NO: 12. Accordingly, in one aspect, the disclosure provides a short chain variable fragment having at least 95% identity to SEQ ID NO: 12, e.g., at least 95% identity, at least 96% identity, at least 97% identity, at least 98% identity, or at least 99% identity to SEQ ID NO: 12. In some embodiments, the short chain variable fragment has a sequence set forth in SEQ ID NO: 12.

In another aspect, the disclosure provides a method of determining the structure of a membrane protein. In one embodiment, the method comprises: (a) providing a complex as described herein; and (b) determining the structure of the complex, to thereby determine the structure of the membrane protein.

The structure of the complex can be determined by X-ray crystallography. In such embodiments, the method may further comprise forming a crystal of the complex.

General methods for the preparation and analysis of protein crystals have been disclosed. For example, see: Alexander McPherson, *Preparation and Analysis of Protein Crystals* (Kreiger Publishing, 1989); Jan Drenth, *Principles of Protein X-Ray Crystallography,* 3rd Ed. (Springer-Verlag, 2007). Briefly, crystal formation can be encouraged by bringing a solution of a protein or complex to supersaturation in a controlled manner; examples of such methods include sitting drop and hanging drop methods. Regulated temperature control may be desirable to improve crystal stability and quality. Temperatures from about 4 to 25° C. can be used during crystal formation, depending on the temperature which is optimal for protein stability over the period of crystal growth. A typical method of determining the three-dimensional structure from the diffraction pattern in X-ray crystallography typically involves multi-wavelength anomalous diffraction (MAD) or multiple isomorphous replacement (MIR) analysis. The X-rays used typically have wavelengths between about 0.9 to 1.7 Å, and are typically produced by synchrotron radiation or with a copper anode X-ray generator.

The structure of the complex can also be determined by electron microscopy. One particular electron microscopy technique useful for protein structure determination is cryo-electron microscopy, in which a protein or complex is flash-frozen in a thin layer, which is then irradiated with low-energy electrons to produce 2D images of individual particles on the detector. General methods for conducting single-particle cryo-electron microscopy have been disclosed. For example, see: Cheng et al. *Cell* 161, 438-449 (2015).

In another aspect, the disclosure provides a use of a peptide having at least 80% identity to a membrane-proximal external region (MPER) sequence from a viral envelope protein for protein structure analysis by fusing the peptide to the terminus of a membrane protein sequence. In some embodiments, the peptide has 14, 15, 16, 17, 18, 19, or 20 amino acids. In some embodiments, the peptide has 17 amino acids. In some embodiments, the peptide has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an MPER sequence from a viral envelope protein. In some embodiments, the viral envelope protein is the human immunodeficiency virus (HIV-1) viral envelope protein gp41, and the MPER has a sequence set forth in SEQ ID NO: 1. In some embodiments, the viral envelope protein is the GP2 subunit of the Ebola virus surface transmembrane glycoprotein (EboV GP2), and the MPER has a sequence set forth in SEQ ID NO: 2. In some embodiments, the viral envelope protein is hemagglutinin (HA) from the influenza B virus, and the MPER has a sequence set forth in SEQ ID NO: 3. In some embodiments, the viral envelope protein is glycoprotein complex E1/E2 from the hepatitis C virus; in some such embodiments, the MPER has a sequence set forth in SEQ ID NO: 4. In some embodiments, the viral envelope protein is gp36 from the feline immunodeficiency virus (FIV), and the MPER has a sequence set forth in SEQ ID NO: 5. In some embodiments, the viral envelope protein is gp41 from the simian immunodeficiency virus (SIV), and the MPER has a sequence set forth in SEQ ID NO: 6. In some embodiments, the viral envelope protein is HR2 from the SARS coronavirus (SARS-CoV) or the SARS coronavirus 2 (SARS-CoV-2), and the MPER has a sequence set forth in SEQ ID NO: 7. Accordingly, in some embodiments, the peptide has at least 80% identity to SEQ ID NO: 1, SEQ ID NO: 2, SEQ ID NO: 3, SEQ ID NO: 4, SEQ ID NO: 5, SEQ ID NO: 6, or SEQ ID NO: 7. In some embodiments, the peptide has a sequence set forth in SEQ ID NO: 1, SEQ ID NO: 2, SEQ ID NO: 3, SEQ ID NO: 4, SEQ ID NO: 5, SEQ ID NO: 6, or SEQ ID NO: 7, or a variant of any thereof having 1, 2, or 3 amino acid substitutions. In some embodiments, one or more of the amino acid substitutions is a conservative substitution. In some embodiments, the peptide is fused to the N-terminus of the membrane protein.

In some embodiments, kits are provided that contain one or more or all of the components necessary, sufficient, or useful for practicing the methods described herein. In some embodiments, the kits comprise one or more expression vectors that encode a viral envelope protein in trans with a cloning site to allow a user to insert a gene of interest encoding a membrane protein into the vector so that a fusion of the membrane protein and viral envelope protein is expressed. In some embodiments, the kit comprises one or more antibody fragments or other molecules that specifically bind the viral envelope protein. In some embodiments, the kits comprise positive and/or negative control reagents. In some embodiments, the kits comprise instructions, which may be written instructions or embodied in a computer readable media. Reagents within the kits may be housed in one or more containers (e.g., tubes) and the collection of kit components may be packaged in one or more boxes or other containers that facilitate shipment and storage of the kit.

The following examples further illustrate aspects of the disclosure but, of course, should not be construed as in any way limiting its scope.

EXAMPLES

In the examples described herein, epitope placement was aided by high resolution structures of the target protein. For the analysis of novel proteins, one skilled in the art will appreciate that additional experimental troubleshooting may be required to determine the proper positioning of the MPER epitope (e.g., along the native TM1 helix). For targets with homology to structurally characterized proteins, or for small membrane proteins with straightforward hydrophobicity profiles, transmembrane helices can be predicted with high accuracy. Thus, epitope placement can be initially predicted, and then experimentally confirmed by shifting the epitope along the TMH1 sequence and testing binding using gel filtration chromatography. Alternatively, for proteins with extracellular N-termini, the extramembrane location of the MPER epitope and membrane compatibility of Fab fragment binding could facilitate rapid in vivo screening of membrane protein expression and testing of MPER fusion registers via cell surface antibody staining. This approach could also be used to increase the mass or improve particle orientation for small, soluble proteins for cryo-EM. For soluble proteins of unknown structure, initial prediction of the fusion site could be less straightforward than for membrane proteins.

Antibody preparation. 10E8v4 antibody expression vector DNA (heavy chain and light chain) was obtained from the NIH AIDS Reagent Program (cat. No. 12866 and 12877). VRC42 and 10E8v4 were prepared according to the same protocol. Heavy and light chain DNA was used to transfect Expi293 HEK cells. Antibodies were harvested from media 5 days post-transfection using Protein A agarose (Pierce). Antibodies were processed to antibody fragments by papain digestion (1:200 antibody: papain), followed by filtration on an immobilized Protein A agarose column (Pierce) to separate Fc domain from Fab fragments. Fab fragments were further purified by gel filtration chromatography.

Negative stain electron microscopy. The target/antibody fragment samples were applied to a glow-discharged, carbon-coated copper grid for 1 minute before removal by blotting. A 0.75% solution of uranyl formate was applied to the grid for 1 minute, followed by removal by blotting and air drying, as previously described (Ohi et al. *Biol. Proced. Online* 6, 23-34 (2004)). Residual stain was removed using a vacuum apparatus. The negatively-stained samples were imaged with a FEI Tecnai T12 microscope operated at 120 keV (MPER-Fluc-Ec2/10E8v4, MPER-Fluc-BPE/VRC42, MPER-AdiC/10E8v4, MPER-GlpF/10E8v4) or a FEI Tecnai T20 microscope operated at 200 keV (MPER-Fluc-Ec2/scFv). Images were acquired with Leginon and SerialEM (Suloway et al. *J. Struct. Biol.* 151, 41-60 (2005); Mastronarde *J. Struct. Biol.* 152, 36-51 (2005)). Images were recorded at a pixel size of 2.34 A/px (MPER-Fluc-Ec2/10E8v4, MPER-GlpF/10E8v4), 1.45 A/px (MPER-Fluc-Bpc/VRC42, MPER-AdiC/10E8v4), or 1.37 A/px (MPER-Fluc-Ec2/10E8v4 scFv). CTF estimation was performed on the images using CTFFIND4 (Rohou et al. *J. Struct. Biol.* 192, 216-221 (2015)) and gCTF (Zhang *J. Struct. Biol.* 193, 1-12 (2016)). Particles were picked using the crYOLO general model (Wagner et al. *Commun. Biol.* 2, 1-13 (2019)). Particle extraction and initial 2D classification was performed using RELION (Zivanov et al. *Elife* 7, e42166 (2018)). Extracted particles were then imported into cryoSparc for 2-D class averaging (Punjani et al. *Nat. Methods* 14, 290 (2017)). Averages were generated using 9,582 (MPER-Fluc-Ec2/10E8v4), 35,096 (MPER-Fluc-BPE/VRC42), 15,290 (PMER-AdiC/10E8v4), 7,594 (MPER-GlpF/10E8v4), and 6,781 (MPER-Fluc-Ec2/10E8v4 scFv) particles. Ab initio models and subsequent 3-D refinements were generated in cryoSPARC (id.). Figures were prepared with UCSF ChimeraX (Goddard et al. *Protein Sci.* 27, 14-25 (2018)).

Example 1

Bioinformatic Evaluation of Membrane Proteins

To assess the suitability of the most membrane-proximal helix of the MPER as a helical tag, small membrane proteins in the protein data bank (PDB) were bioinformatically evaluated for their ability to accept the MPER epitope tag as graft for the N-terminus of the first transmembrane helix (TMH1) in order to create a chimera between the epitope tag and membrane protein.

α-helical transmembrane proteins from the non-redundant PDB-TM database, excluding theoretical models, were obtained from the RCSB Protein Data Bank (934 proteins). Transmembrane biological units were reconstructed from α-helical transmembrane chains identified in "biological unit" information from REMARK 350 of the PDB file. For complexes with a molecular weight of ≤100 kDa (457 proteins), the membrane was modelled using the PPM2.0 method (see the Orientations of Proteins in Membranes (OPM) database, https://opm.phar.umich.edu), implemented using a known program (Lomize et al. *Nucleic Acids Res.,* 40 (2012), pp. D370-D376). Based on the estimated membrane boundaries, the dataset was further filtered to include only complexes with two or more transmembrane helices and with more than 50% of residues inside the membrane. The proteins in this set (304 proteins) were analyzed for steric compatibility with the MPER epitope tag according to two criteria: a tilt angle for the first transmembrane helix of ≥45° relative to the plane of the membrane (294 proteins), and no clashes between the MPER epitope tag and the target protein. To assess clashes between the target protein and MPER, the last 8 residues of the α-helical MPER peptide (LWNWFDITNWLWYIKSLAAAA) were aligned in PyMol with the first TM helix of the target protein in four registers: n (the first eight residues of the first transmembrane helix of the target), n+1, n+2, and n+3. Each of these four models was assessed for clashes (Cα≤3 Å) between the MPER epitope tag and the biological unit. Models with an acceptable tilt angle for TM helix 1, and with no clashes between MPER and the target protein (1069 models representing 290 proteins) were further assessed for complexation by antibody fragments 10E8 Fab, 10E8 scFv, 4E10 Fab, and 4E10 scFv. For each model, the antibody fragment was positioned relative to the MPER epitope based on structures of antibody-MPER complexes (PDB: 1TZG (Cardoso et al. *Immunity,* 22 (2005), pp. 163-173) and PDB: 5JNY (Soto et al. *PLoS ONE,* 11 (2016) e0157409) and assessed for clashes (Cα≤5 Å) with the target protein, the membrane, or, for targets with oligomeric construction, other antibody fragments. For these calculations, the residues N-terminal to the twelfth residue of the target's first transmembrane helix were not considered. To assess membrane clashes, the membrane boundary was extended to the length of the antibody complex, and the membrane-penetrating CDR loops of the antibody fragments were excluded from the calculation. Different cutoffs for MPER and antibody clashes calculations were chosen because the MPER clash reflects intra-protein interactions, whereas the antibody clash reflects inter-protein interactions. All models that could accommodate at least one of the four antibody fragments with <10 clashes were manually inspected. A workflow and examples of models that do and do not satisfy each condition is available in FIG. 9, and analysis of the models sorted according to the sequence position of the first TM helix is shown in Table 1. All models are available Supplementary Data for download from the Deep Blue Data repository hosted by the University of Michigan, with unique identifier https://doi.org/10.7302/7ym7-gp78.

TABLE 1

Models for MPER-membrane protein fusions and antibody binding analyzed according to the sequence position of the first residue of TM helix 1

| Step | TMH1 start at residue position 1-25 | 26-50 | >50 |
|---|---|---|---|
| 50% protein inside membrane | 280 | 20 | 4 |
| Tilt of TMH1 <=45° | 270 | 20 | 4 |
| Can accept MPER tag | 266 | 20 | 4 |
| Tolerate 4e10 or 10e8 Fv/Fab | 87 | 9 | 1 |
| Tolerate 4e10 or 10e8 Fv/Fab (minor clash) | 61 | 4 | 0 |

Figure 2:
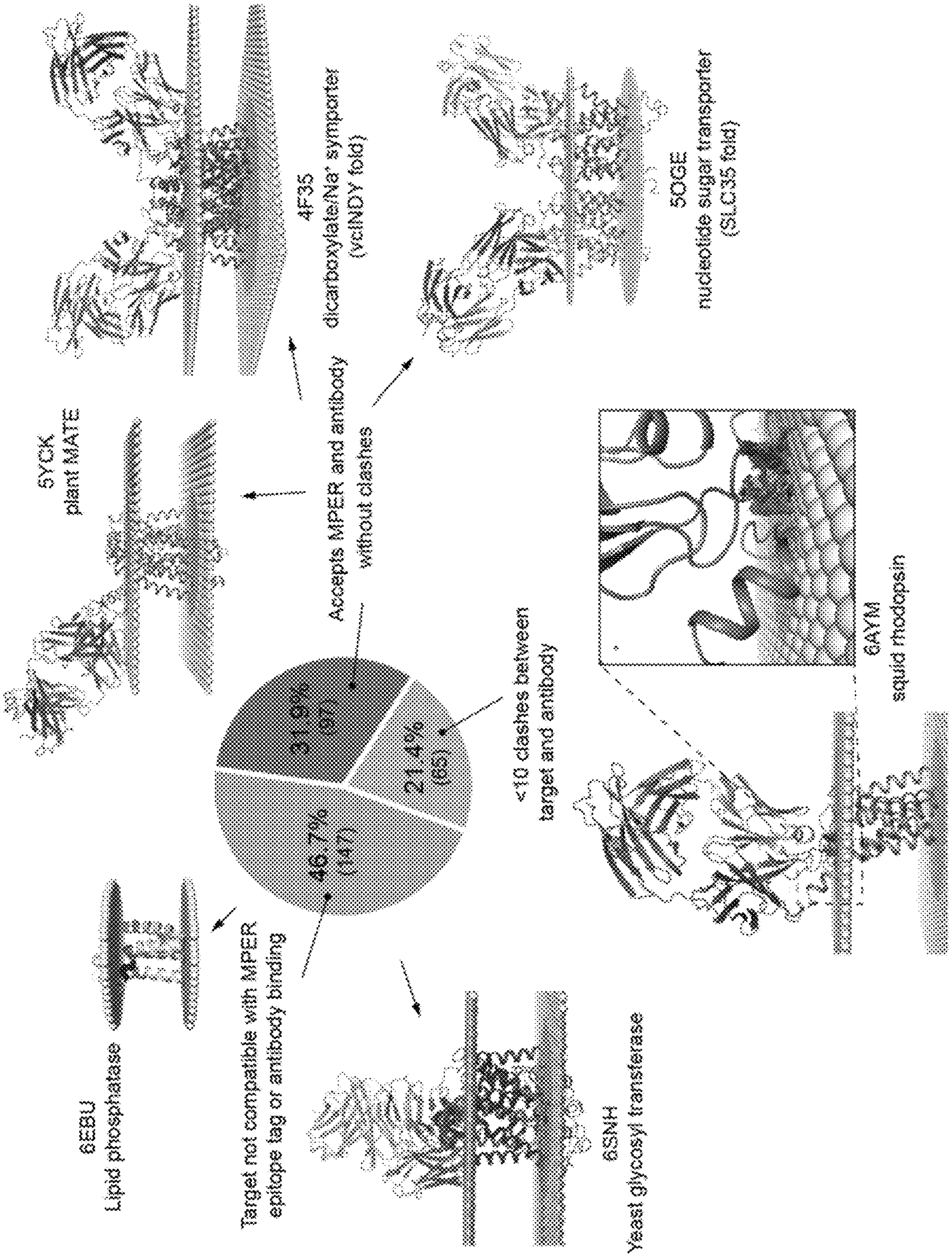
FIG. 2 shows information regarding a bioinformatic analysis of MPER fusion and antibody binding to small membrane proteins (see Example 1 for details). For targets in dataset, pie chart shows the percentage (total number in parentheses) that is (i) compatible with MPER fusion and 10E8v4 or 4E10 antibody fragment binding; (ii) compatible with MPER fusion and antibody binding with <10 clashes between target and antibody fragment; (iii) not compatible with this strategy because the target's first TM helix is at an oblique angle to the membrane or bound Fab clashes with target. For each category, example models are shown.

Small membrane proteins that lack extracellular domains were a focus of evaluation, since these are particularly difficult to characterize using standard structural techniques. 304 unique structures of membrane proteins smaller than 100 kDa were identified, with at least two transmembrane helices and at least half of all residues embedded in the membrane. Of these proteins, 89% were found to be sterically compatible with such an N-terminal helix graft. For those membrane proteins structurally compatible with the MPER epitope tag, antibody fragments 10E8 and 4E10 were analyzed for whether they could bind to the tag in one of several registers without clashing with the target protein or the membrane. The analysis suggests that over half of unique small membrane proteins in the PDB, representing diverse folds, are likely to be structurally compatible with the N-terminal helix tag and its recognition by an MPER-binding antibody fragment (FIG. 2).

Example 2

Fusion Protein Preparation

Sequences encoding the fluoride channel from *E. coli* (Fluc-Ec2), the fluoride channel from *Bordetella pertussis* (Fluc-Bpe), the arginine/agmatine antiporter from *S. entericus* (AdiC), and the aqua-glycerol channel from *E. coli* (GlpF) were cloned into a protein expression vector (pET21a), C-terminal to an N-terminal hexahistidine tag, a thrombin cleavage site, and a sequence encoding the HIV-1 gp41 MPER epitope (LWNWFDITNWLWYIKNL—SEQ ID NO: 1). The constructs were designed so that the MPER sequence was positioned at the membrane boundary. *E. coli* C41 cells transformed with this plasmid were grown at 37° C. to an $O.D_{600}$ of ~1 before induction with isopropyl β-1-thiogalactopyranoside (IPTG) at 37° C. for 1-3 hours. The Fluc-Ec2 and Fluc-Bpe variants were induced for 1 h with 4 mM isopropyl β-1-thiogalactopyranoside (IPTG); the GlpF variant was induced for 2 h with 1 mM IPTG; the AdiC variant was induced for 1 h with 0.2 mM IPTG. Cells were harvested by centrifugation, resuspended in cell breaking buffer (100 mM NaCl, 20 mM Tris pH 8.0) with lysozyme (1 mg/mL), protease inhibitor cocktail (Roche), PMSF (200 mM), and lysed by sonication on ice. After detergent extraction with 2% n-Decyl-β-D-Maltoside (DM) for 2 hours, cell debris were removed by centrifugation, and His-tagged proteins were isolated using cobalt affinity resin (Takara). Bound protein was eluted with 400 mM imidazole, and applied to a desalting column to remove imidazole. His tags were cleaved with overnight thrombin digestion (1.58 U thrombin per mg protein, 4° C.).

Sequences of the three fusion proteins are set forth in SEQ ID NO: 8 (MPER-Fluc-Ec2), SEQ ID NO: 9 (MPER-Fluc-Bpe), SEQ ID NO: 10 (MPER-GlpF), and SEQ ID NO: 11 (MPER-AdiC).

For antibody complexation, protein and 10E8v4 Fab were combined in a 1:1 stoichiometric ratio 2 hours at room temperature prior to gel filtration (Superdex200 equilibrated in 100 mM NaCl, 10 mM HEPES pH 7.5, 4 mM DM). Fractions corresponding to the protein: 10E8v4 Fab complex were isolated and used for further studies.

Example 3

MPER-Fluc-Bpe Fusion Protein Complexation

The fluoride channels from the Fluc family are small (30-kDa) structurally characterized membrane proteins involved in bacterial resistance to fluoride ions. Homologues from *Bordetella pertussis* (Fluc-Bpe) and *E. coli* (Fluc-Ec2) have been structurally characterized (Stockbridge et al. *Nature* 525, 548-551 (2015); McIlwain et al. Structure 26, 635-639 e1 (2018), each of which is herein incorporated by reference in its entirety). The channels are assembled as antiparallel dimers, with each monomer comprised of four transmembrane helices. Based on the known structure of the Fluc channels, the MPER epitope was genetically fused to the N-terminal end.

Figures 3A, 3B, 3C, 3D:
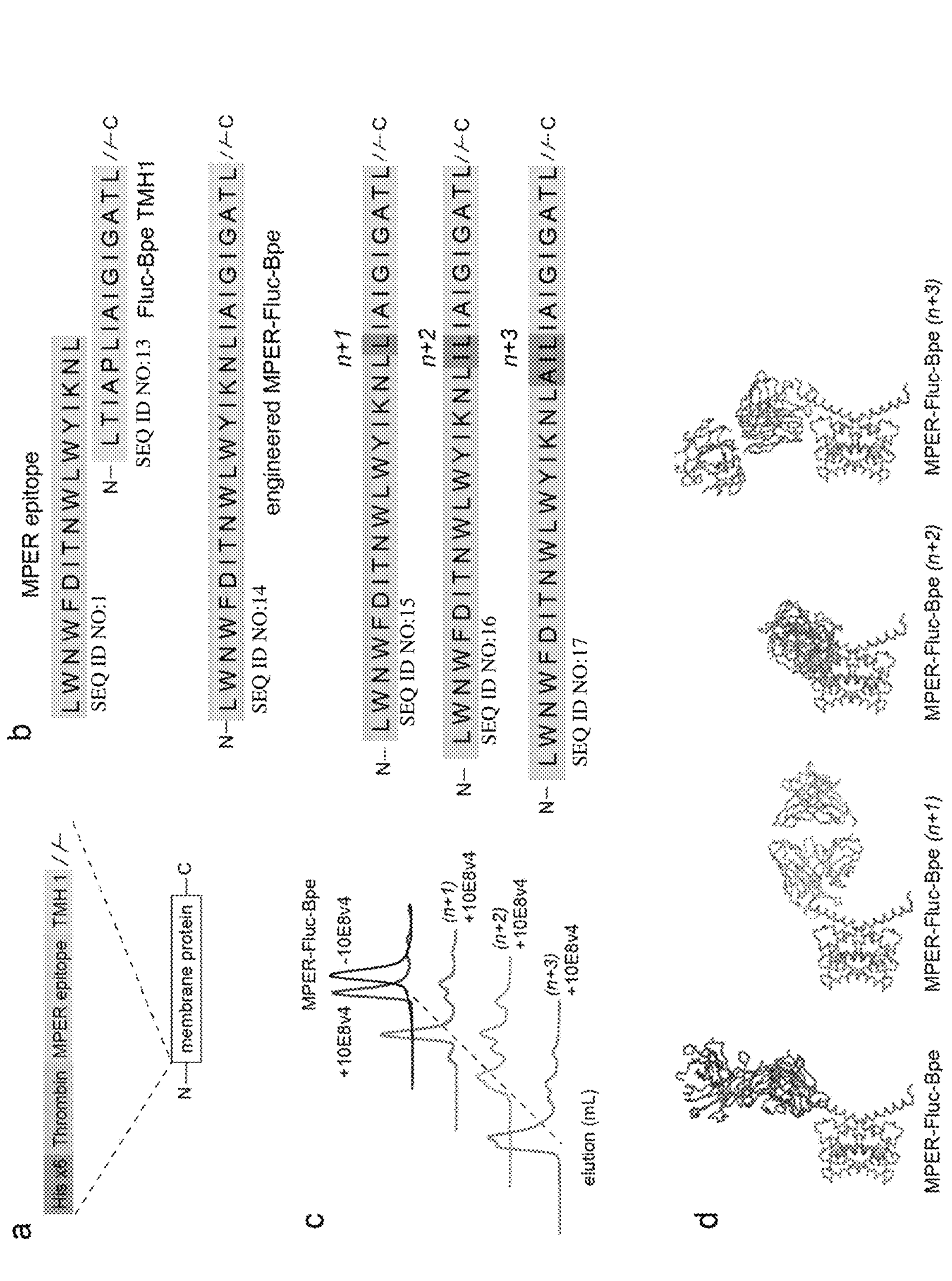
FIGS. 3*a*-3*d* show information and data for a fluoride channel membrane protein fusion with a MPER epitope tag, as described in Examples 2 and 3: (a) design of the construct with the MPER sequence fused to the fluoride channel from *B. pertussis* (Fluc-Bpe); (b) alignment of MPER sequence to Fluc-Bpe TMH1 sequence, starting at residue 2 (N-terminal methionine not shown); (c) Left: comparison of gel filtration profiles of four MPER-Bpe fusion proteins; the top trace shows MPER-Fluc-Bpe alone and in complex with 10E8v4. Subsequent traces show comparison of gel filtration profiles of MPER-Fluc-Bpe fusion proteins in complex with 10E8v4, with the position of the MPER epitope shifted N-terminally by the indicated number of amino acids. Right: sequences of register-shifted constructs; (d) bioinformatic models showing how the Fluc-Bpe/10E8v4 interface would be expected to change for each construct.

The MPER-Fluc-Bpe fusion protein (FIG. 3A and FIG. 3B) was prepared as described in Example 1. After protein purification and cleavage of the His tag with thrombin, the protein yield for MPER-Fluc-Bpe was slightly better than that of wild-type Fluc-Bpe (1.5 mg protein/L *E. coli* culture). MPER-Fluc-Bpe fusion protein was incubated with the MPER-binding antibody Fab fragment 10E8v4, a variant of the human-isolated 10E8 antibody that has been engineered for greater stability and solubility (Kwon et al. *J. Virol.* 90, 5899-5914 (2016)). Gel filtration chromatography revealed a 2-mL shift in the retention time of the protein fraction, confirming the formation of a stable MPER-Fluc-Bpe/10E8v4 complex (FIG. 3C).

Additional MPER-Fluc-Bpe constructs were expressed and purified, with the sequence for the MPER epitope shifted along the TMH1 sequence (n+1, n+2, n+3). When purified individually, these MPER-Fluc-Bpe fusion proteins were monodisperse. However, when these MPER fusion proteins were complexed with 10E8v4 Fab fragments, the protein did not elute as a single peak, indicating that these constructs would not be suitable for further structural work (FIG. 3C). FIG. 3*d* shows models of the complexes with the helical epitope shifted N-terminally along TMH1 (n+1, n+2, n+3), assuming a rigid-body rotation/translation of the Fab together with its binding site. Thus, the MPER epitope should be engineered into the proper position with respect to the three-dimensional structure of the membrane protein to facilitate antibody fragment binding, and the correct positioning can be experimentally determined by systematically shifting the register of the fusion.

Example 4

MPER-Fluc/10E8v4 Antibody Fragment Crystallography

For structural analysis, SEC-purified complexes of MPER-Fluc-BPE or MPER-Fluc-Ec2 and 10E8v4 were prepared for vapor diffusion crystallography. Samples containing stable MPER-Fluc-Ec2/10E8v4 complex were concentrated to 10 mg/mL and mixed with an equal volume of crystallization solution in 24-well sitting-drop vapor diffusion trays. After optimization of initial hits, MPER-Fluc-Ec2/10E8v4 crystals grew in 100 mM NaCl, 34-39% PEG 300, 100 mM MES pH 6.2-7.0. For MPER-Fluc-Ec2/scFv crystallization, the stable complex was formed as for MPER-Fluc-Ec2/10E8v4, and protein samples were mixed with an equal volume of crystallization solution from commercial screening blocks (MemGold and MemGold2, Molecular Dimensions) in 96 well plates. The best-diffracting crystals were grown in 100 mM calcium acetate, 100 mM HEPES pH 7.5, 33.8% PEG 600. Crystals were frozen in liquid nitrogen prior to data collection at the Life Sciences Collaborative Access Team beamline 21-ID-D at the Advanced Photon Source, Argonne National Laboratory. Data were somewhat anisotropic, but ellipsoidal truncation did not improve the maps, so the data were spherically truncated so that data completeness was maximized (99%) in the highest resolution shell. Phases were calculated by molecular replacement with Phaser (McCoy et al. *J. Appl. Crystallogr.,* 40 (2007), pp. 658-674) using Fluc-Ec2 (pdb: 5A43) (Stockbridge 2015) and the constant and variable domains of 10E8v4 (pdb: 5IQ9) (Kwon 2016) as search models. The MPER peptide was built into the Fo-Fc difference density map, followed by iterative rounds of refinement with Refmac (Murshudov et al. *Acta Crystallogr. D Biol. Crystallogr.,* 67 (2011), pp. 355-367) or Phenix (Liebschner et al. *Acta Crystallogr. D Struct. Biol.,* 75 (2019), pp. 861-877) and model building in real space with Coot (Emsley et al. *Acta Crystallogr. D Biol. Crystallogr.,* 66 (2010), pp. 486-501). Models were validated using Molprobity (Williams et al. *Protein Sci.,* 27 (2018), pp. 293-315) and by preparing composite omit maps, with 5% of the atoms omitted from the model at a time using Phenix (Terwilliger et al. *Acta Crystallogr. D Biol. Crystallogr.,* 64 (2008), pp. 515-524). Figures were prepared with PyMol.

Figures 4A, 4B, 4C:
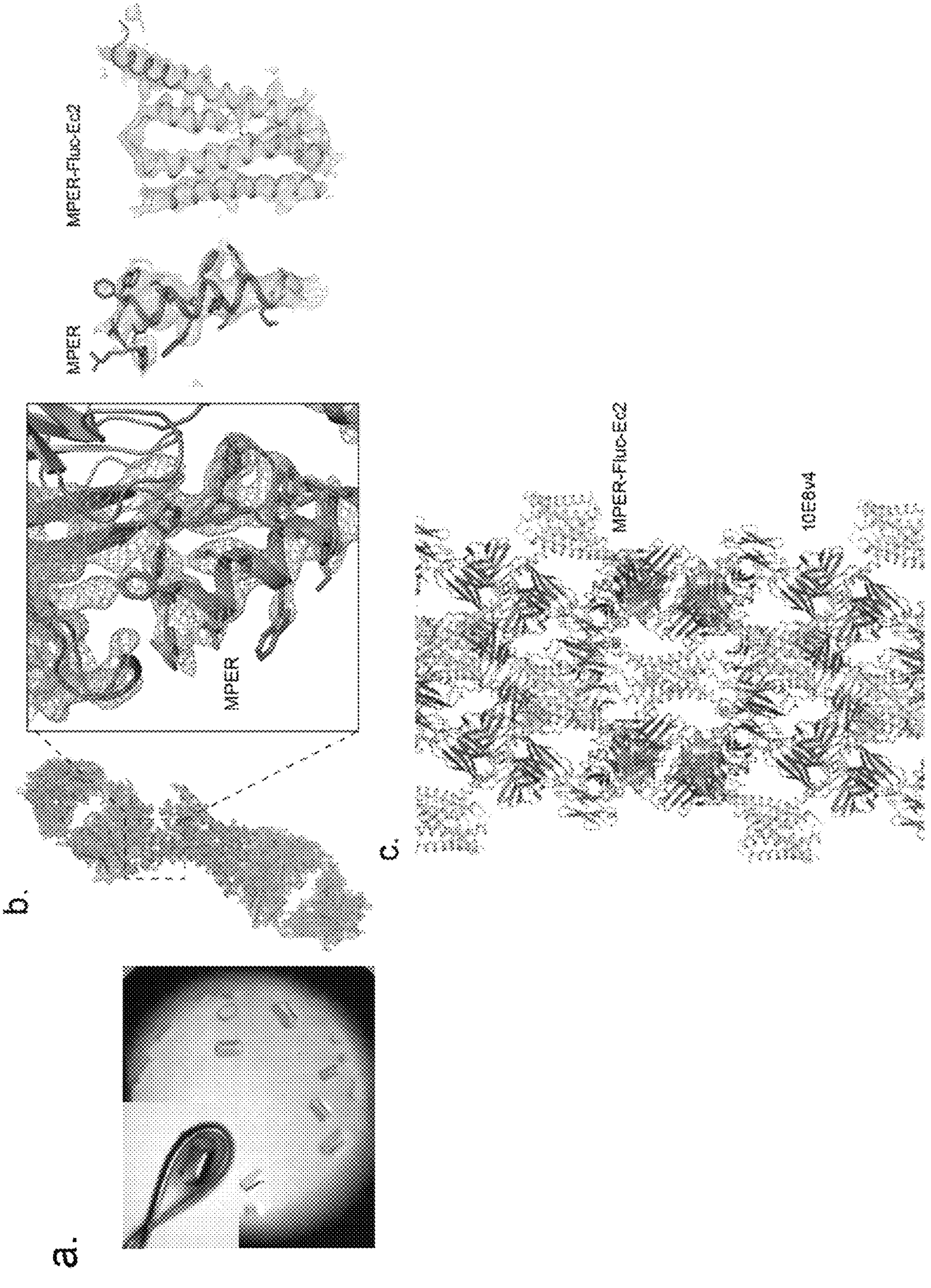
FIGS. 4*a*-4*c* show data for structural characterization of the Fluc-Ec2/10E8v4 complex: (a) MPER-Fluc-Ec2/10E8v4 crystals; (b) Left, X-ray crystallographic model of MPER-Fluc-Ec2/10E8v4 complex, with 2Fo-Fc map contoured at 1.0 σ; right: 2Fo-Fc composite omit maps for MPER peptide and MPER-Fluc-Ec2 monomer calculated from the MPER-Ec2/10E8v4 data. Maps were calculated omitting 5% of the atoms in the model at a time, contoured at 1.0 σ; (c) MPER-Fluc-Ec2/10E8v4 crystal lattice

For Fluc-Ec2 and Fluc-Bpe, previous structure determination had required complexation with soluble crystallography chaperones called monobodies. They diffracted to resolutions of 2.2-3.5 Å, depending on the monobody chaperone (McIlwain et al. Structure, 26 (2018) 635-9 e1; Stockbridge et al. *Nature* 525, 548-551 (2015). Alone, the channels, which are almost entirely membrane-embedded, do not even form crystals, despite extensive screening (Stockbridge 2015). In contrast, in trays set with the MPER-Fluc-Ec2/10E8v4 complex, crystals began to form within 24-hours and reached a maximum size of ~200 μm in approximately one week (FIG. 4*a*). These crystals diffracted to 3.3 Å Bragg spacing. The structure was solved using molecular replacement, with one monomer of Fluc-Ec2 and one 10E8v4 Fab fragment per asymmetric unit (FIG. 4*b*, left panel, and Table 2). Initial maps showed unambiguous Fo-Fc density that defined the MPER peptide (FIG. 4*b*). Both the MPER/Fab binding interface and the overall orientations of the Fluc channel and the Fab fragments closely matched a model for the complex (Cα RMSD=1.4 Å). The solvent content of this crystal and the average β-factors for this structure are high (average B-factor=160 Å2), limiting the resolution especially in the TM3-TM4 of Fluc-Ec2. The average B-factor for the residues 96-126 ($C_\alpha$) of chain E, comprising TM4 for that Fluc protomer, was ~270 Å2, equivalent to a mean square displacement for each residue of ~1.8 Å. Nevertheless, all four helices from the channel are clearly visible in composite omit maps (FIG. 4*b*, right panel), and maps show unambiguous density for the side-chains of the MPER epitope (FIG. 4*b*). Strikingly, MPER-Fluc-Ec2 made no contribution to the crystal lattice, with crystal contacts instead formed exclusively by the 10E8v4 Fab fragments bound to each side of the antiparallel Fluc-Ec2 dimer (FIG. 4*c*).

TABLE 2

X-ray crystallography data collection and refinement statistics.

| | MPER-Fluc-Ec2/10E8v4 |
|---|---|
| **Data collection** | |
| Space group | $P3_2$ |
| Cell dimensions | |
| a, b, c (Å) | 99.1, 99.1, 167.6 |
| α, β, γ (°) | 90, 90, 120 |
| Resolution (Å) | 38.18-3.26 (3.46-3.26) |
| Data Completeness | 98.6 (98.4) |
| $R_{merge}$ | 0.135 (2.44) |
| $R_{meas}$ | 0.141 (2.56) |
| Mn I/σI | 10.3 (1.0) |
| $CC_{1/2}$ | 0.999 (0.765) |
| Multiplicity | 10.8 (11.2) |
| **Refinement** | |
| Resolution (Å) | 34.0-3.26 |
| No. reflections | 26, 788 |
| $R_{work}/R_{free}$ | 25.1/29.5 |
| Ramachandran Favored | 90.3 |
| Ramachandran Outliers | 2.0 |
| Clashscore | 10.1 |
| R.m.s. deviations | |
| Bond lengths (Å) | 0.003 |
| Bond angles (°) | 0.72 |

Example 5

Negative Stain EM Analysis of MPER-Fluc in Complex with Antibody Fragments

Figures 5A, 5B:
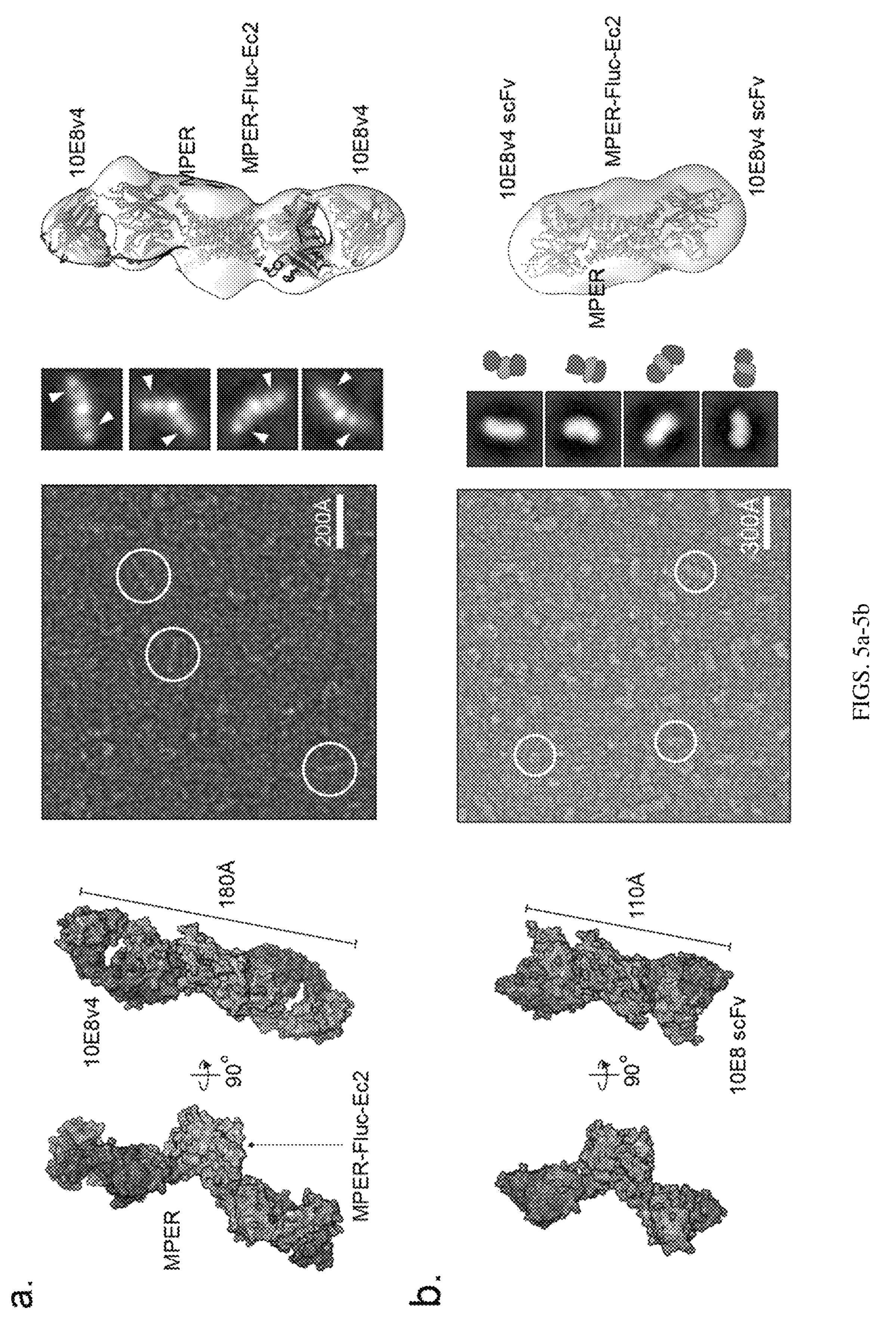
FIGS. 5*a*-5*b* show: (a) left panel: MPER-Fluc-Ec2/10E8v4 crystal structure shown as surface representation, with the dimensions of the expected particles shown; middle: representative negative stain micrograph and 2-D class averages of MPER-Fluc-Ec2/10E8v4 complex, where the scale bar represents 200 Å, and white arrows indicate bound antibody fragments with characteristic "hole" between the heavy and light domains, box size 398 Å; right, 3-D ab initio reconstruction of particles, where the density envelope has been fitted with the crystal structure from FIG. 4; (b) left panel: MPER-Fluc-Ec2/scFv model shown as surface representation, with the dimensions of expected particles shown; middle: representative negative stain micrograph and 2-D class averages of MPER-Fluc-Ec2/scFv complex; scale bar 300 Å, box size, 398 Å; cartoons are provided as interpretations of the orientation of each class average; right: 3-D reconstruction of particles, where the density envelope has been fitted with a bioinformatic model of the MPER-Fluc-Ec2/scFv complex.

MPER-Fluc-Ec2/10E8v4 sample was applied to a carbon-coated grid and negatively stained, as described above (Ohi 2004). The raw micrographs of MPER-Fluc-Ec2 bound to 10E8v4 antibody fragments showed elongated particles that measured approximately 180 Å in the longest dimension (FIG. 5*a*). 2-D class averages revealed particles with strong central density flanked by Fab fragment clamshells at each end (FIG. 5*a*, middle panel). The reconstructed 3-D volume closely corresponded to the expected particle shape and size based on the crystal structure (FIG. 5*a*, right panel), with clearly resolved holes between the constant and variable domains for both bound fragments.

When MPER-Fluc-Ec2 was complexed with 10E8v4-scFv instead, negative stain electron microscopy revealed discrete 3-unit particles that appeared shorter than the MPER-Fluc-Ec2/10E8v4 Fab particles observed previously, in agreement with the expected architecture of the MPER-Fluc-Ec2 dimer bound to two molecules of scFv (FIG. 5*b*).

Example 6

Single Particle Cryo-EM of MPER-Fluc in Complex with VRC42 Fab

VRC42 Fab and MPER-Fluc-Bpe, at 0.5 mg/mL, in a buffer of 100 mM NaCl, 10 mM HEPES pH 7.5, 4 mM DM, were combined in a molar ratio 0.3:1. 3.5 µL of 0.5 mg/mL solution of the complex was applied to glow discharged (5 mA 30 s) Quantifoil R1.2/1.3 200 mesh copper grids (Electron Microscopy Sciences). The sample was blotted 1 time for 2 s with blot force 1 and then plunged into liquid ethane using a Vitrobot Mark IV (Thermo Fisher Scientific) set at 100% humidity/4° C. Samples were clipped and loaded into a Talos *Arctica* transmission electron microscope (Thermo Fisher Scientific) operating at 200 kV with a gun lens of 6, a spot size of 6, 70 µm C2 aperture, and 100 µm objective aperture. Frames were collected on a K2 direct electron detector (Gatan) in counting mode at 45,000 kx corresponding to a pixel size of 0.91 Å/px. Leginon was used for automated data acquisition. Each movie had a total dose of approximately 65-70 e/Å$^2$ with a defocus range of −1.0 µm to 3.0 µm.

3911 movies were aligned using MotionCor2 (Zheng et al. *Nat. Methods,* 14 (2017), pp. 331-332). CTFFIND4 was used to estimate CTF values for aligned micrographs (Rohou 2015). Micrographs with poor CTF fits were discarded. Two datasets (1965 movies total) were collected and combined in downstream processing steps. For Dataset 1, 30,899 particles were picked manually and 2D classification was performed on extracted particles using cryoSPARC v2.15.0 (Punjani et al. *Nat. Methods,* 14 (2017), p. 290). The resulting 2-D class averages were used as templates for template-based picking in cryoSPARC v2.15.0 (Punjani 2017) and the best 2-D class averages (22,699 particles) were used to generate 3 ab initio reconstructions. 232,123 particles were picked with template-based picking and extracted for 2D classification. After selecting particles from the best 2-D classes, 191,230 particles were used for heterogeneous refinement into 3 classes using the 3 ab initio reconstructions generated previously as reference volumes. 1 class with 65,654 particles (34% of particles) with strong density for VRC42 protruding from MPER-Fluc-Bpe in DM. For Dataset 2, 963,331 particles were picked with template-based picking and extracted for 2D classification. After selecting particles from the best 2-D classes, 65,882 particles were then combined with the 65,654 particles from Dataset 1 and underwent 2 rounds of multi-reference ab initio reconstruction to isolate MPER-Fluc-Bpe bound to a single VRC42 Fab fragment. This resulted in a particle stack with 35,655 particles that was used for 3D homogeneous refinement. The final map was deposited into the Electron Microscopy Data Bank under accession number EMD-23247.

Figures 6A, 6B, 6C, 6D:
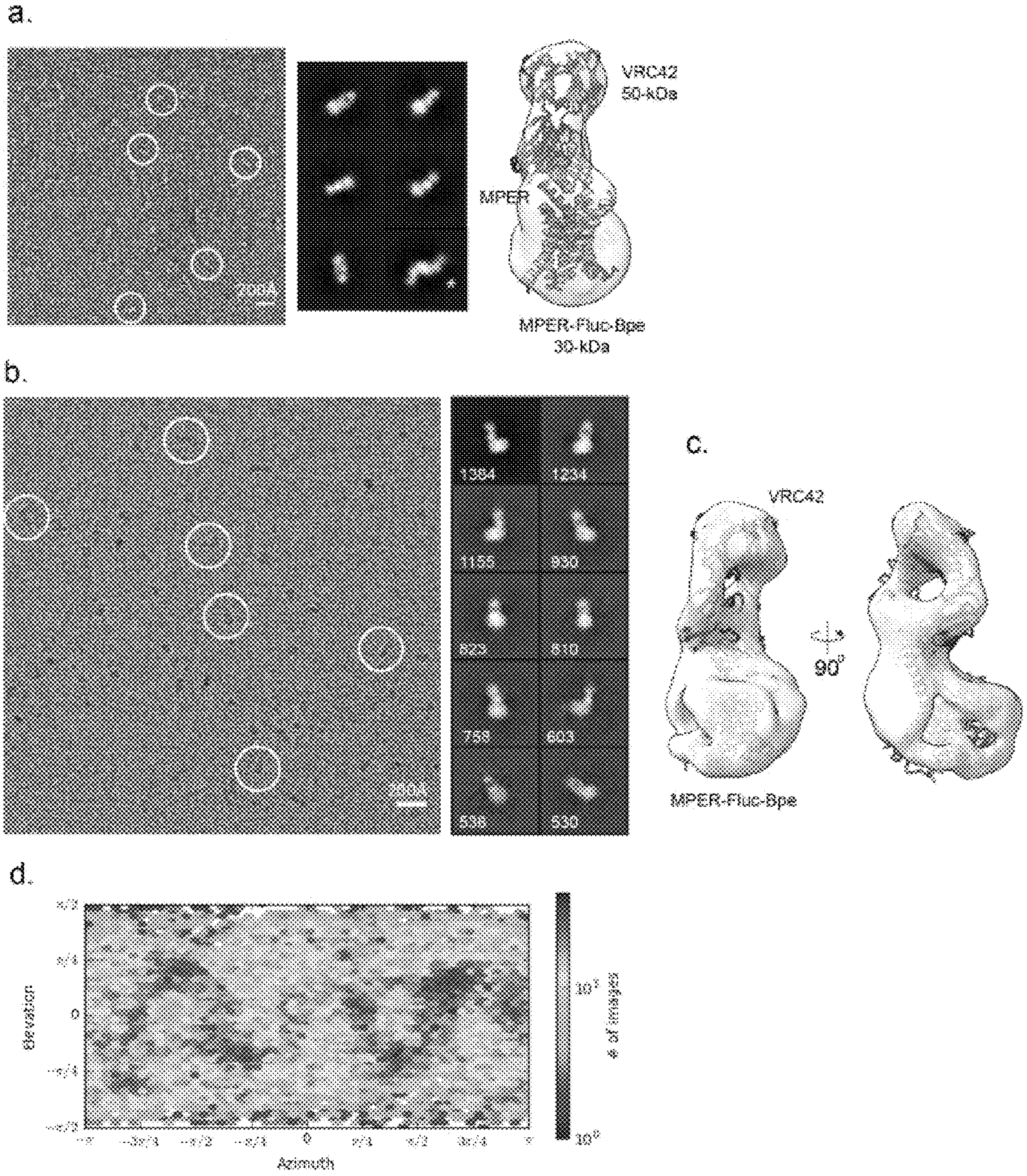
FIGS. 6*a*-6*d* show data for the cryo-EM analysis of MPER-Fluc-Bpe in complex with VRC42: (a) representative negative stain micrograph (left) and 2-D class averages (middle) of MPER-Fluc-Bpe/VRC42 complex (1 dimer: 0.3 Fab molar ratio), scale bar 200 Å, box size 320; the asterisk denotes the doubly-occupied class, which included 2.5% of total particles; right: 3-D reconstruction of negative stain particles, where the density envelope has been fitted with bioinformatic model based on crystal structures of Fluc-Bpe (pdb: 5NKQ) and VRC42 (pdb: 6MTQ); (b) representative cryo-EM micrograph and 2-D class averages of MPER-Fluc-Bpe/VRC42 in vitreous ice, where the number of particles present in each class are displayed, scale bar 200 Å, box size 328 Å; (c) 3-D cryo-EM reconstruction of particles, where the density envelope has been fitted with model; (d) distribution of viewing angles for particles used in reconstruction.

The Fluc channels are unusual among membrane proteins in that the antiparallel subunits present epitopes on both sides of the membrane, so that the doubly-Fab-bound particles are disproportionately long and thin. This doubly-bound species might require thicker, contrast-poor ice or adopt a preferred orientation in the vitrified ice layer. The stoichiometric ratio of membrane protein and antibody fragment was therefore also varied. Some samples included equal molar ratios of membrane protein and Fab so that the MPER epitopes were fully occupied. In other samples, a dimer was used: Fab molar ratio of 1:0.3. At this ratio, assuming that MPER occupancy by Fab follows random statistical capture, only 3% of Fluc channels are expected to be doubly occupied, with the singly occupied species ~10-fold more prevalent. The substantial portion of unoccupied, 30 kDa Fluc particles were anticipated to be difficult to visualize and behave as "background." Negative stain EM of one of these sub-stoichiometric preparations, MPER-Fluc-Bpe/VRC42, was conducted as described above. It confirmed the expected distribution of singly- and doubly bound particles (FIG. 6*a*). Three-dimensional reconstructions based on the negative stain data captured the expected difference in VRC42 binding orientation compared to 10E8v4.

Out of these various combinations of Fluc homologue, Fab identity, and Fab occupancy, initial screening experiments showed that the preparation of MPER-Fluc-Bpe/VRC42 with predominately singly bound particles was well-behaved in vitreous ice (FIG. 6*b*, left). Particles were not clearly detected for the other preparations, and would require additional screening. 2D classes from approximately 30,000 manually picked particles were used as input for template-based picking. Multiple rounds of 2D classification yielded 2-D class averages of MPER-Fluc-Bpe complexed with a single VRC42 Fab fragment in multiple orientations (FIG. 6*b*, right). Following iterative 3D classifications and a final homogeneous refinement, a final map with 35,655 single Fab-bound particles resolved to approximately 16 Å. (FIG. 6*c*, Table 3). This low-resolution electron density map matches the expected particle shape and size of a Fluc-Bpe channel in a detergent micelle bound to a single VRC42 Fab fragment (FIG. 6*c*). Approaching high resolution for MPER-Fluc-Bpe would likely require a concerted campaign of biochemical optimization (for example reconstitution into nanodiscs), hardware optimization (for example use of phase plates to enhance contrast), a much larger dataset, and/or additional data processing maneuvers including different masking strategies. These experiments presented here demonstrate two favorable traits for cryo-EM structural analysis: the MPER-channel/Fab complex is stable in vitreous ice, and the particles are well-distributed over all possible Euler angles (FIG. 6*d*).

TABLE 3

Cryo-EM data collection and processing

| | MPER-Fluc-Bpe/VRC42 | |
|---|---|---|
| Dataset | 1 | 2 |
| Sample | MPER-Fluc-Bpe/VRC42 (0.3:1 molar ratio) | |
| Grid Type | Quantifoil 1.2/1.3 200 mesh | |
| Microscope | Thermo Fischer Talos Arctica | |
| Camera | Gatan K2 | |
| Voltage | 200 kV | |
| Total electron exposure | 65 e-/Å$^2$ | |
| Defocus range | −1.5-3.5 μm | |
| Pixel Size | 0.91 Å/pix | |
| Micrographs | 2,131 | 1780 |
| Micrographs Used | 1076 | 889 |
| Refined Particles (masked monomer) | 35,655 | |
| Resolution | ~10 Å | |

Example 7

MPER-GlpF Complexation and Characterization

To test whether membrane proteins with disparate folds could host the MPER epitope tag and bind Fab in the predicted orientation, MPER fusions for two additional structurally characterized, biochemically tractable targets representing different protein folds were designed: AdiC, a bacterial arginine/agmatine exchanger that possesses the LeuT-fold (Fang et al. *Nature,* 460 (2009), pp. 1040-1043), and GlpF, a bacterial glycerol channel that possesses the aquaporin fold (Fu et al. *Science* 290, 481-6 (2000)). Negative stain EM (conducted as described above) was used to determine whether Fab could bind to these MPER-tagged proteins, and to assess the homogeneity of the resulting complex formation (FIG. 7).

Figures 7A, 7B, 7C, 7D, 7E, 7F:
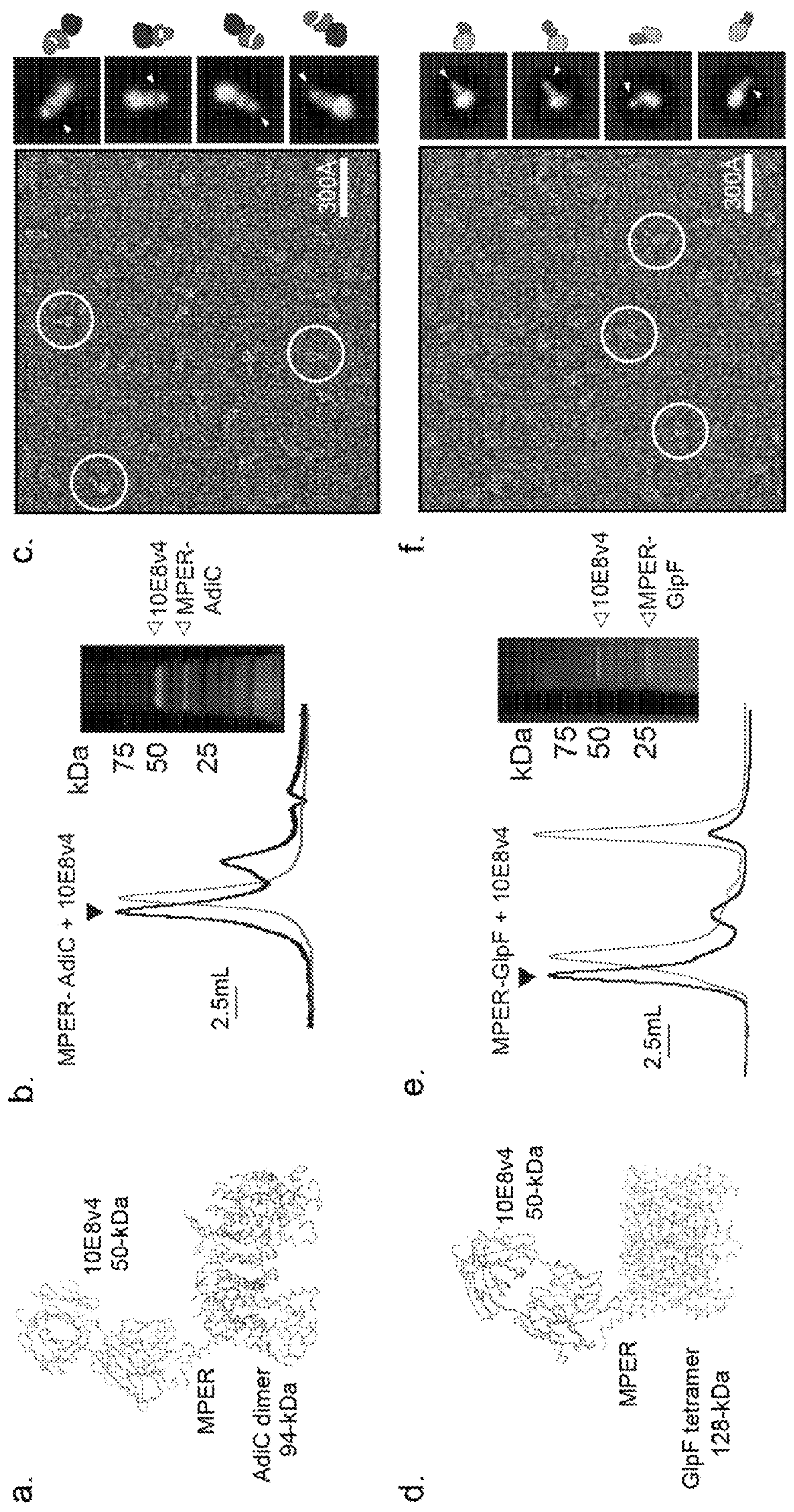
FIGS. 7*a*-7*f* show data for 10E8v4 binding to AdiC and GlpF bearing an MPER epitope tag: (a) model of AdiC fused with the MPER epitope and bound to 10E8v4 Fab; model based on crystal structures of AdiC (pdb: 3NCY) and 10E8v4; (b) left, gel filtration chromatograms of MPER-AdiC alone and MPER-AdiC/10E8v4 complex; right, SDS-PAGE gel of the indicated fraction with major components labeled; (c) representative negative stain micrograph and 2-D class averages of MPER-AdiC/10E8v4; cartoons of the AdiC dimer (and 10E8v4 Fab are shown below each average to assist in interpretation of the orientation; white arrows indicate 10E8v4 Fab, scale bar 300 Å, box size 319 Å; (d) model of GlpF tetramer fused with the MPER epitope and bound to 10E8v4 Fab, with the model based on known structures of GlpF (pdb: 1FX8) and 10E8v4; (e) left: gel filtration chromatograms of MPER-GlpF alone the MPER-GlpF/10E8v4 complex; right: SDS-PAGE gel of the indicated fraction with major components labeled; (f) representative negative stain micrograph and 2-D class averages of MPER-GlpF/10E8v4; cartoon representations of GlpF bound to 10E8v4 Fab shown below each class average to assist in interpretation of the orientation; white arrows indicating 10E8v4 Fab, scale bar 300 Å, box size 468 Å.

The AdiC protein from *Salmonella enterica* is a biological dimer with ten TMHs per subunit. Each subunit is approximately 47-kDa in size. Based on the crystal structure (Fang 2009), the placement of the helical MPER epitope was modeled so that Fab fragment binding to this epitope would not clash with the extracellular portions of the transporter (FIG. 7*a*). The model suggested that 10E8v4 Fab binding to the first epitope of the AdiC dimer might preclude binding of a second Fab to the second epitope. Indeed, when Fab and AdiC were mixed in varying molar ratios, the relative integrated areas of the elution peaks for the AdiC: 10E8v4 complex and 10E8v4 was consistent with a 1 AdiC dimer: 1 Fab molar ratio (and inconsistent with either an AdiC dimer: 2 Fab complex or an AdiC monomer: 1 Fab complex). When MPER-AdiC was mixed with Fab at a molar ratio of 1 Fab per MPER-AdiC dimer, the MPER-AdiC/10E8v4 complex eluted as a single monodisperse peak 0.5 mL earlier than AdiC alone (FIG. 7*b*). SDS-PAGE analysis of this fraction confirmed that both MPER-AdiC and the 10E8v4 Fab were present in this peak (FIG. 7*b*). Further analysis with negative stain electron microscopy revealed particles consistent with a globular membrane protein bound to a Fab fragment; in some of the 2-D class averages the hole between constant and variable domains is readily visible (FIG. 7*c*).

GlpF is a 28-kDa aquaglycoporin that permits diffusion of glycerol and some linear polyalcohols in *E. coli*, and is composed of six membrane-spanning TMHs and two re-entrant haripins. GlpF alone crystallized as a tetramer (id.), but biochemical studies have suggested that the oligomer is weakly associated and that monomeric proteins are both frequently observed (Manley et al. *Biochemistry* 39, 12303-11 (2000); Borgnia et al. *Proc. Natl. Acad. Sci. USA* 98, 2888-93 (2001)) and functional (Trefz et al. *Biochim. Biophys. Acta Biomembr.* 1860, 887-894 (2018); Cymer et al. *Biochemistry* 49, 279-86 (2010)). As with MPER-Fluc-Ec2 and MPER-AdiC, modelling suggested that MPER-GLPF would bind to 10E8v4 without steric clashes (FIG. 7*d*). The MPER-GlpF fusion protein and its complex with 10E8v4 Fab were prepared as described in Example 1.

GlpF was mixed with a sub-stoichiometric concentration of 10E8v4 Fab. The resultant MPER-GlpF/10E8v4 complex elutes from the size exclusion column as a single monodisperse peak that contains both protein components at an elution volume approximately 1 mL earlier than GlpF alone (FIG. 7*e*). Analysis with negative stain electron microscopy (conducted as described above) showed well-dispersed particles, with characteristic Fab density readily visible in both raw micrographs and 2-D class averages (FIG. 7*f*). The particle shape and size are consistent with a GlpF monomer bound to a single Fab fragment.

Example 8

Design and Purification of a Single-Chain Variable-Domain Antibody Fragment (scFv)

Design of scFv (FIG. 8*a*, SEQ ID NO: 12) was aided by the crystal structure of 10E8v4 bound to the helical epitope.

The construct was designed as: Heavy $Chain_{variable}$-$(Gly_3Ser)_4$ linker-Light $Chain_{variable}$-TEV cleavage site-His ×6 and sub-cloned into the periplasmic expression vector pET26b. *E. coli* (Origami B (DE3), Novagen) bearing this construct was grown at 37° C. until reaching an $O.D_{600}$ of ~0.8, induced with 50 μM IPTG and induced overnight at 16° C. Cells were harvested and resuspended in osmotic shock buffer (200 mM Tris pH 8, 5 mM EDTA, 20% sucrose) and incubated for 1 hour at room temperature with occasional mixing. Cell suspension was centrifuged (16,000 r.p.m) to pellet the bacterial cytoplasm and cellular debris. Supernatant containing scFv was purified using gel filtration (Superdex 200 equilibrated in 100 mM NaCl, 10 mM HEPES pH 7.5, 4 mM DM).

Figures 8A, 8B, 8C, 8D, 8E:
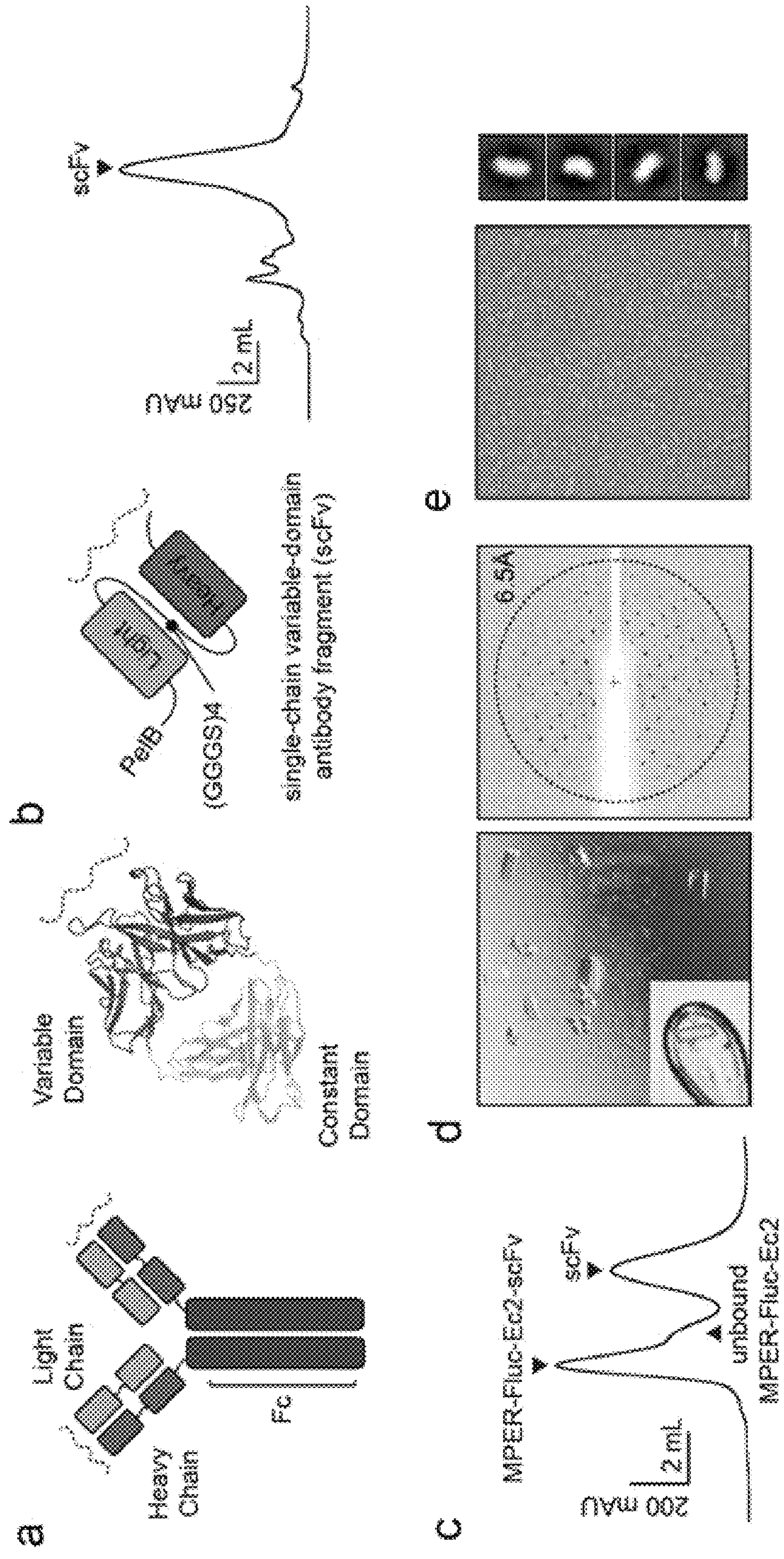
FIGS. 8*a*-8*e* show design and data for a single-chain variable-domain antibody fragment (scFv) based on 10E8v4: (a) Left, cartoon of full-length antibody (IgG) with the heavy and light chains that comprise the Fab fragment labeled; Right, Fab fragment with the constant domain and epitope-binding variable domain labeled, with epitope binding surface represented by a dashed line; (b) Left, scFv design; Right, gel elution profile of bacterial periplasmic supernatant with scFv peak indicated; (c) Gel elution chromatogram of MPER-Fluc-Ec2 incubated with scFv; (d) Crystals of MPER-Fluc-Ec2/scFv grown in sitting drop format, and resulting diffraction pattern; (e) Representative negative stain micrograph and 2-D class averages of MPER-Fluc-Ec2/scFv complex, scale bar 200 Å, box size 398 Å.

The protein was expressed (FIG. 8*b*) with a yield of ~3 mg/L *E. coli* culture. Purified 10E8-scFv was soluble and monodisperse, and bound stably to MPER-Fluc-Ec2 as shown with size exclusion chromatography (FIG. 8*c*). Like the full-length 10E8v4 Fab fragment, the 10E8-scFv promoted crystallization of the Fluc proteins, which do not crystallize in the absence of soluble chaperones (Stockbridge 2015). Crystals formed after approximately 3 days in several conditions from a commercial screening block. Initial hits diffracted to 6.5 Å Bragg spacing (FIG. 8*d*); and although further optimization would be required to solve the structure of this complex by X-ray crystallography, these results show that the variable domain alone can act as a crystallization chaperone for MPER-membrane protein fusions. In addition, these samples were imaged by negative stain electron microscopy. The particles observed were in agreement with the expected architecture of the MPER-Fluc-Ec2 dimer bound to two molecules of scFv: discrete 3-unit particles (FIG. 8*e*) that appeared shorter than the MPER-Fluc-Ec2/10E8v4 Fab particles observed previously.

| SEQUENCES |
|---|
| HIV-1 gp41 MPER (SEQ ID NO: 1): LWNWFDITNWLWYIKNL |
| Ebola virus GP2 MPER (SEQ ID NO: 2): DNDNWWTGWRQWIIAGIG |
| Influenza B virus MPER (SEQ ID NO: 3): TQ(Q/S/K)AIDQI(T/N)GKLNR |
| Hepatitis C virus MPER (SEQ ID NO: 4): TGLIHLHQNIVDVQYLY |
| Feline immunodeficiency virus MPER (SEQ ID NO: 5): WEDWVGWIGNIIQY |
| Simian immunodeficiency virus MPER (SEQ ID NO: 6):<br>KLNSWDVFGNWFDLASWIKYIQ |
| SARS coronavirus/coronavirus-2 MPER (SEQ ID NO: 7):<br>Y(V/I)KWPW(W/Y)VWLGF |
| MPER-Fluc-Ec2 fusion protein (SEQ ID NO: 8):<br>GHHHHHHGGLVPRGSASLWNWFDITNWLWYIKNLIAVIIGGSVGCTLRWLLSTRFNSLF<br>PNLPPGTLVVNLLAGLIIGTALAYFLRQPHLDPFWKLMITTGLCGGLSTFSTFSVEVFALL<br>QAGNYIWALTSVLVHVIGSLIMTALGFFIITILFA |
| MPER-Fluc-Bpe fusion protein (SEQ ID NO: 9):<br>GHHHHHHGGLVPRGSASLWNWFDITNWLWYIKNLIAIGIGATLGAWLRWVLGLRLNG<br>AGWPWGTLTANLVGGYLIGVMVALIASHPEWPAWIRLAAVTGFLGGLTTFSTFSAETV<br>DMLERGVYATAAAYAGASLAGSLAMTGLGLATVRLLLR |
| MPER-GlpF fusion protein (SEQ ID No: 10):<br>GHHHHHHGGLVPRGSASLWNWFDITNWLWYIKNLIAEFLGTGLLIFFGVGCVAALKVA<br>GASFGQWEISVIWGLGVAMAIYLTAGVSGAHLNPAVTIALWLFACFDKRKVIPFIVSQV<br>AGAFCAAALVYGLYYNLFFDFEQTHHIVRGSVESVDLAGTFSTYPNPHINFVQAFAVEM<br>VITAILMGLILALTDDGNGVPRGPLAPLLIGLLIAVIGASMGPLTGFAMNPARDFGPKVF<br>AWLAGWGNVAFTGGRDIPYFLVPLFGPIVGAIVGAFAYRKLIGRHLPCDICVVEEKETTT<br>PSEQKASL |
| MPER-AdiC fusion protein (SEQ ID NO: 11):<br>GHHHHHHSGGLVPRGSGSLWNWFDITNWLWYIKNLIALIIVTLMVSGNIMGSGVFLLPA<br>NLAATGGIAIYGWLVTIIGALALSMVYAKMSSLDPSPGGSYAYARRCFGPFLGYQTNVL<br>YWLACWIGNIAMVVIGVGYLSYFFPILKDPLVLTLTCVAVLWIFVLLNIVGPKMITRVQA<br>VATVLALVPIVGIAVFGWFWFKGETYMAAWNVSGMNTFGAIQSTLNVTLWSFIGVESA<br>SVAAGVVKNPKRNVPIATIGGVLIAAVCYVLSTTAIMGMIPNAALRVSASPFGDAARMA<br>LGDTAGAIVSFCAAAGCLGSLGGWTLLAGQTAKAAADDGLFPPIFARVNKAGTPVAGL<br>LIVGVLMTIFQFSSMSPNAAKEFGLVSSVSVIFTLVPYLYTCAALLLLGHGHFGKARPLY<br>LLITFVAFVYCIWAVIGSGAKEVMWSFVTLMVITALYALNYNRIHKNPYPLDAPVKQD |
| scFv protein sequence (SEQ ID NO: 12):<br>GWSCIILFLVATATGVHSEVRLVESGGGLVKPGGSLRLSCSASGFDFDNAWMTWVRQP<br>PGKGLEWVGRITGPGEGWSVDYAESVKGRFTISRDNTKNTLYLEMNNVRTEDTGYYFC<br>ARTGKYYDFWSGYPPGEEYFQDWGQGTLVIVSSASGGGGSGGGGSGGGGSGGSGWSCI<br>ILFLVATATGSVTASELTQDPAVSVALKQTVTITCRGDSLRSHYASWYQKKPGQAPVLL<br>FYGKNNRPSGIPDRFSGSASGNRASLTITGAQAEDEADYYCSSRDKSGSRLSVFGGGTKL<br>TVLSQPKAAENLYFQSHHHHHH |
| Fluc-BPE Transmembrane Helix 1 (SEQ ID NO: 13): LTIAPLIAIGIGATL |
| Engineered MPER-Fluc-BPE sequence (SEQ ID NO: 14):<br>LWNWFDITNWLWYIKNLIAIGIGATL |

-continued

| SEQUENCES |
| --- |
| Engineered MPER-Fluc-BPE sequence (n + 1) (SEQ ID NO: 15):<br>LWNWFDITNWLWYIKNLLIAIGIGATL |
| Engineered MPER-Fluc-BPE sequence (n + 2) (SEQ ID NO: 16):<br>LWNWFDITNWLWYIKNLILIAIGIGATL |
| Engineered MPER-Fluc-BPE sequence (n + 3) (SEQ ID NO: 17):<br>LWNWFDITNWLWYIKNLAILIAIGIGATL |

The invention claimed is:

1. A complex comprising:

(a) a MPER peptide fusion protein comprising formula A-B, wherein:

A is a peptide having consisting of the sequence of SEQ ID NO: 1; and

B is membrane protein; and (b) an antibody fragment that binds to the peptide A.

2. The complex of claim 1, wherein B is a membrane protein having a molecular weight of less than 200 kDa.

3. The complex of claim 1, wherein A is attached to the N-terminus of the membrane protein B.

4. The complex of claim 1, wherein the antibody fragment is a Fab fragment from an antibody selected from the group consisting of 10E8, LN01, DH511, VRC42, PGZL1, and 4E10.

5. The complex of claim 4, wherein the antibody fragment is a Fab fragment from an antibody selected from the group consisting of 10E8 and VRC42.

6. A method of determining the structure of a membrane protein, comprising:

(a) providing a complex of claim 1; and (b) determining the structure of the complex by X-ray crystallography or electron microscopy, to thereby determine the structure of the membrane protein.

7. The method of claim 6, wherein the structure of the complex is determined by X-ray crystallography.

8. The method of claim 7, further comprising a step of forming a crystal of the complex.

9. The method of claim 6, wherein the structure of the complex is determined by electron microscopy.

10. The method of claim 9, wherein the electron microscopy is cryo-electron microscopy.

* * * * *